United States Patent
Poston et al.

(10) Patent No.: US 7,998,128 B2
(45) Date of Patent: Aug. 16, 2011

(54) ACTIVE DELIVERY AND FLOW REDIRECTION: NOVEL DEVICES AND METHOD OF DELIVERY OF MATERIALS TO PATIENTS

(75) Inventors: David Poston, Bungay (GB); Raghu Raghavan, Baltimore, MD (US); Martin L. Brady, Phoenix, MD (US)

(73) Assignee: Therataxis, LLC., Baltimore, MD (US)

( * ) Notice: Subject to any disclaimer, the term of this patent is extended or adjusted under 35 U.S.C. 154(b) by 709 days.

(21) Appl. No.: 11/434,080

(22) Filed: May 15, 2006

(65) Prior Publication Data
US 2007/0276340 A1    Nov. 29, 2007

(51) Int. Cl.
*A61M 31/00* (2006.01)
(52) U.S. Cl. ............... 604/506; 604/500; 604/513
(58) Field of Classification Search ............. 604/101.01, 604/101.05, 103.03, 116, 164.01, 174, 500, 604/506, 508, 509, 511, 513, 514, 523, 93.01, 604/96.01, 507, 908, 912, 915
See application file for complete search history.

(56) References Cited

U.S. PATENT DOCUMENTS

| | | | | |
|---|---|---|---|---|
| 3,896,816 A * | 7/1975 | Mattler | ................. | 604/103.03 |
| 4,807,620 A | 2/1989 | Strul et al. | ................ | 606/28 |
| 4,824,436 A | 4/1989 | Wolinsky | ................ | 604/509 |
| 4,892,538 A | 1/1990 | Aebischer et al. | ......... | 604/891.1 |
| 4,941,874 A | 7/1990 | Sandow et al. | ................. | 604/60 |
| 4,973,304 A | 11/1990 | Graham et al. | ................ | 604/48 |
| 5,017,566 A | 5/1991 | Bodor | ................... | 514/58 |
| 5,082,670 A | 1/1992 | Gage et al. | .................. | 424/520 |
| 5,087,256 A | 2/1992 | Taylor et al. | ................. | 606/28 |
| 5,106,627 A | 4/1992 | Aebischer et al. | ............. | 424/424 |
| 5,120,322 A | 6/1992 | Davis et al. | ................... | 604/265 |
| 5,167,625 A | 12/1992 | Jacobsen et al. | .......... | 604/891.1 |
| 5,171,217 A | 12/1992 | March et al. | .................. | 604/507 |
| 5,195,526 A * | 3/1993 | Michelson | ................... | 600/431 |
| 5,226,902 A | 7/1993 | Bae et al. | ................... | 604/892.1 |
| 5,328,456 A * | 7/1994 | Horiguchi et al. | ............. | 604/22 |
| 5,487,739 A | 1/1996 | Aebischer et al. | ......... | 604/890.1 |
| 5,514,092 A | 5/1996 | Forman et al. | ........... | 604/101.03 |
| 5,569,197 A | 10/1996 | Helmus et al. | ........... | 604/102.02 |
| 5,571,089 A | 11/1996 | Crocker | ................... | 604/103.01 |
| 5,573,668 A | 11/1996 | Grosh et al. | ................. | 210/490 |
| 5,580,575 A | 12/1996 | Unger et al. | ................. | 424/450 |
| 5,607,418 A | 3/1997 | Arzbaecher | ............... | 604/891.1 |

(Continued)

OTHER PUBLICATIONS

"Relux-free cannula for convection-enhanced high speed delivery of therapeutic agents" by Michal T. Krauze, et al. Journal of Neurosurgery, vol. 103, pp. 923-929, 2005.

*Primary Examiner* — Theodore J Stigell
*Assistant Examiner* — Shefali D Patel
(74) *Attorney, Agent, or Firm* — Mark A. Litman & Assoc. PA

(57) ABSTRACT

A medical device for delivering material through tissue into a defined area of a patient may comprise: a material delivery element through which the material may flow out of a delivery end; the delivery end having an opening that can be inserted through a surface of the tissue; and a sealing system proximal to the delivery end that can extend away from the material delivery element along the surface of the tissue and apply pressure to the tissue after the material delivery element has been inserted through the surface of the tissue. A physical barrier may be provided on the material delivery device to reduce back flow loss of delivered material.

11 Claims, 25 Drawing Sheets

U.S. PATENT DOCUMENTS

| | | | |
|---|---|---|---|
| 5,697,946 A * | 12/1997 | Hopper et al. | 606/185 |
| 5,762,926 A | 6/1998 | Gage et al. | 424/93.21 |
| 5,843,048 A | 12/1998 | Gross | 604/264 |
| 5,865,728 A * | 2/1999 | Moll et al. | 600/204 |
| 5,964,705 A | 10/1999 | Truwit et al. | 600/423 |
| 6,026,316 A | 2/2000 | Kucharczyk et al. | 600/420 |
| 6,059,734 A * | 5/2000 | Yoon | 600/565 |
| 6,061,587 A | 5/2000 | Kucharczyk et al. | 600/411 |
| 6,263,237 B1 * | 7/2001 | Rise | 607/3 |
| 6,506,378 B1 | 1/2003 | Kang | 424/93.21 |
| 6,537,232 B1 | 3/2003 | Kucharczyk et al. | 600/561 |
| 6,626,902 B1 | 9/2003 | Kucharczyk et al. | 606/41 |
| 6,656,152 B2 * | 12/2003 | Putz | 604/96.01 |
| 6,663,857 B1 | 12/2003 | Barba et al. | 424/93.21 |
| 6,749,833 B2 | 6/2004 | Raghavan et al. | 424/9.1 |
| 6,950,699 B1 * | 9/2005 | Manwaring et al. | 600/547 |
| 2002/0019623 A1 | 2/2002 | Altman et al. | 604/508 |
| 2002/0188167 A1 * | 12/2002 | Viole et al. | 600/16 |
| 2003/0014016 A1 * | 1/2003 | Purdy | 604/174 |
| 2003/0097116 A1 | 5/2003 | Putz | 604/509 |
| 2003/0202990 A1 * | 10/2003 | Donovan et al. | 424/239.1 |
| 2005/0085790 A1 * | 4/2005 | Guest et al. | 604/506 |
| 2007/0060973 A1 * | 3/2007 | Ludvig et al. | 607/45 |

\* cited by examiner

Catheter Insertion Guidelines which the insertion is unhappily along a sulcus, and the other in which it is transverse to one.

Sylvian Fissure

Temporal/Occipital Lobe

>2.5 cm

>0.5 cm

Figure 19. Infusion of 1:200 Gd-DTPA:water solution. Four T1-weighted 3D SPGR slices, 3mm separation. The infusion catheter is visible in the first slice (left). Subsequent slices reveal leakage and spread of the infusate into the subarachnoid space.

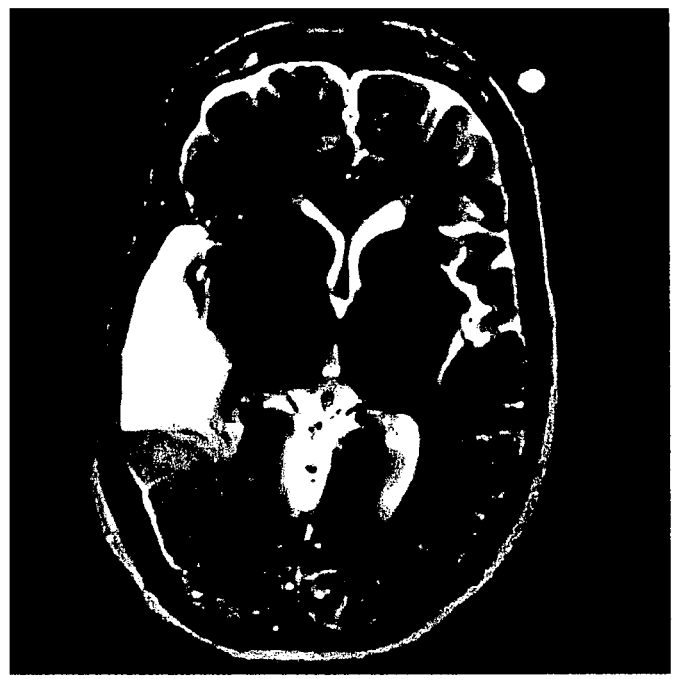
FIG. 21
FIG. 22
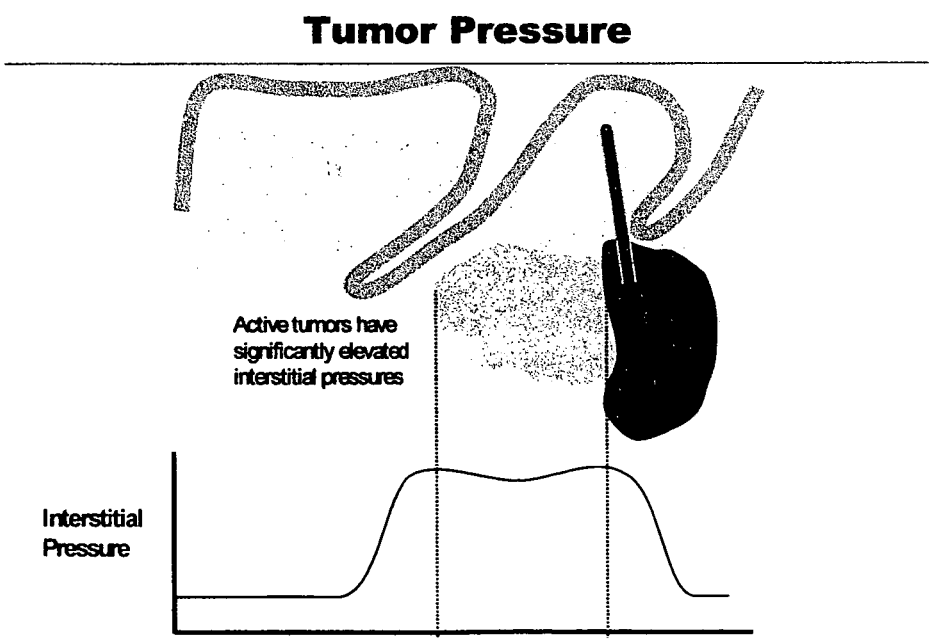

FIG. 23
Tumor Infusion, catheter near enhancing rim

ACTIVE DELIVERY AND FLOW REDIRECTION: NOVEL DEVICES AND METHOD OF DELIVERY OF MATERIALS TO PATIENTS

FEDERAL FUNDING AND RIGHTS DATA

This Application is based in part on work done under Federal Contract No. 6R43NS048695-02 from the National Institute of Health, with the U.S. government accordingly retaining limited rights thereto.

BACKGROUND OF THE INVENTION

1. Field of the Invention

The present invention relates to the field of medical procedures, particularly invasive medical procedures, and more particularly invasive medical procedures to the brain.

2. Background of the Art

The brain is found inside the bony covering called the cranium. The cranium protects the brain from injury. Together, the cranium and bones that protect our face are called the skull. Meninges are three layers of tissue that cover and protect the brain and spinal cord. From the outermost layer inward they are: the dura mater, arachnoid and pia mater. In the brain, the dura mater is made up of two layers of whitish, inelastic (not stretchy) film or membrane. The outer layer is called the periosteum. An inner layer, the dura, lines the inside of the entire skull and creates little folds or compartments in which parts of the brain are neatly protected and secured. There are two special folds of the dura in the brain, the falx and the tentorium. The falx separates the right and left half of the brain and the tentorium separates the upper and lower parts of the brain.

The second layer of the meninges is the arachnoid. This membrane is thin and delicate and covers the entire brain. There is a space between the dura and the arachnoid membranes that is called the subdural space. The arachnoid is made up of delicate, elastic tissue and blood vessels of different sizes. The layer of meninges closest to the surface of the brain is called the pia mater. The pia mater has many blood vessels that reach deep into the surface of the brain. The pia, which covers the entire surface of the brain, follows the folds of the brain. The major arteries supplying the brain provide the pia with its blood vessels. The space that separates the arachnoid and the pia is called the subarachnoid space. A clear fluid may often lie within the interface between the pia and the next adjacent layer.

Cerebrospinal fluid, also known as CSF, is found within the brain and surrounds the brain and the spinal cord. It is a clear, watery substance that helps to cushion the brain and spinal cord from injury. This fluid circulates through channels around the spinal cord and brain, constantly being absorbed and replenished. It is within hollow channels in the brain, called ventricles, where the fluid is produced. A specialized structure within each ventricle, called the choroid plexus, is responsible for the majority of CSF production. The brain normally maintains a balance between the amount of cerebrospinal fluid that is absorbed and the amount that is produced. Often, disruptions in the system occur.

Although various forms of interventional and drug therapy procedures have been performed on the brain since the time of the Pharaohs in Egypt, significant technical advances in procedures are essential to the improvement of success in such procedures. Even as drug delivery to regions of the brain by localized invasive procedures has become available, the procedures still need to be refined for different regions, different drugs, and new and effective methodologies of delivery become desirable.

The pia has been generally treated as a barrier or annoyance in accessing or treating areas of the brain during surgery and procedures have been generally performed without any attempt to use the presence of the pia as a benefit. See for example, the procedures in Journal of Neuroscience, Volume 16, Number 18, Issue of Sep. 15, 1996 pp. 5864-5869; *Interaction of Perirhinal Cortex with the Fornix-Fimbria: Memory for Objects and 'Object-in-Place' Memory*, David Gaffan and Amanda Parker.

U.S. Pat. Nos. 6,663,857; 6,506,378; 5,762,926 and 5,082,670 describe graft procedures wherein a graft may be placed in a ventricle, e.g. a cerebral ventricle or subdurally, i.e. on the surface of the host brain where it is separated from the host brain parenchyma by the intervening pia mater or arachnoid and pia mater. Grafting to the ventricle may be accomplished by injection of the producer cells or by growing the cells in a substrate such as 30% collagen to form a plug of solid tissue which may then be implanted into the ventricle to prevent dislocation of the graft. For subdural grafting, the cells may be injected around the surface of the brain after making a slit in the dura. Injections into selected regions of the host brain may be made by drilling a hole and piercing the dura to permit the needle of a microsyringe to be inserted. The microsyringe is preferably mounted in a stereotaxic frame and three dimensional stereotaxic coordinates are selected for placing the needle into the desired location of the brain.

U.S. Pat. No. 5,843,048 (Gross) describes syringe tip designs for use in epidural applications. The designs include straight epidural needles employed in the former procedure do not require the passage of a catheter. These typically have a straight distal end and a gauge size on the order of 21-22 gauge (iso-9626); while those of the latter type, through which a catheter is introduced, of necessity are somewhat larger, having a gauge size typically on the order of 17-18 gauge (iso-9626). The needles of the latter type, used for introducing a catheter into the epidural space, are described as possessing a curved tip so that the distal end of the catheter can curve upward for proper placement within the epidural space rather than perpendicularly abutting the dura mater, the delicate membrane lying over the arachnoid and pia mater covering the spinal cord.

U.S. Pat. No. 6,626,902 (Kucharczyk et al.) describes new hardware for delivery of drugs intraparenchymally and to regions of the brain in particular comprising a multi-lumen, multi-functional catheter system. The system comprises a plurality of axial lumens, at least one lumen supporting material delivery of primary treatment chemistry to a point of release and a second lumen having a component supporting a functionality electrostatically near the point of release other than material delivery and material removal wherein at least one biological or physiological measuring device is present within at least one lumen in which information from said at least one biological or physiological measuring device is connected to a host computer and said information is received by said host computer, wherein the component provides information other than information from said at least one biological or physiological measuring device and the component is connected to a host computer and said information is received by said host computer.

U.S. Pat. No. 6,537,232 (Kucharczyk et al.) describes a device and method for monitoring intracranial pressure during magnetic resonance (MR) image-guided neurosurgical procedures, such as intracranial drug delivery procedures, wherein an MR-compatible microsensor pressure transducer coupled to a pressure sensing diaphragm located a) at the tip, b) on a lateral side, and/or c) in multiple locations of an MR-compatible catheter is inserted into a lateral cerebral ventricle, cerebral cistern, subarachnoid space, subdural or extradural spaces, venous sinuses, or intraparenchymal tissue locations under MR imaging guidance, and is used to record intracranial pressures over hours to days in patients undergoing diagnostic or therapeutic neurologic interventions.

"Reflux-free cannula for convection-enhanced high speed delivery of therapeutic agents" by Michal T. Krauze et. al. Journal of Neurosurgery, vol. 103, pp 923-929, 2005 describes a two-lumen design called a step cannula in which a thin cannula projects of a larger lumen. The design is claimed to prevent backflow (see description of irreducible backflow below).

The standard current procedure for drug treatment of various focal neurological disorders, neurovascular diseases, and neurodegenerative processes requires neurosurgeons or interventional neuroradiologists to deliver drug agents by catheters or other tubular devices directed into the cerebrovascular or cerebroventricular circulation, or by direct injection of the drug agent, or cells which biosynthesize the drug agent, into targeted intracranial tissue locations. The blood-brain barrier and blood-cerebrospinal fluid barrier almost entirely exclude large molecules like proteins, and control entry of smaller molecules. Small molecules (<200 Daltons) which are lipid-soluble, not bound to plasma proteins, and minimally ionized, such as nicotine, ethanol, and some chemotherapeutic agents, readily enter the brain. Water soluble molecules cross the barriers poorly or not at all. Delivery of a drug into a ventricle bypasses the blood-brain barrier, and allows for a wide distribution of the drug in the brain ventricles, cisterns, and spaces due to the normal flow pathways of cerebrospinal fluid in the brain. However, following intracerebroventricular injection, many therapeutic drug agents, particularly large-molecular weight hydrophobic drugs, fail to reach their target receptors in brain parenchyma because of metabolic inactivation and inability to diffuse into brain tissues, which may be up to 18 mm from a cerebrospinal fluid surface.

To optimize a drug's therapeutic efficacy, it should be delivered to its target tissue at the appropriate concentration. A number of studies reported in the medical literature, for example, Schmitt, Neuroscience, 13, 1984, pp. 991-1001, have shown that numerous classes of biologically active drugs, such as peptides, biogenic amines, and enkephalins have specific receptor complexes localized at particular cell regions of the brain. Placing a drug delivery device directly into brain tissue thus has the notable advantage of initially localizing the injected drug within a specific brain region containing receptors for that drug agent. Targeted drug delivery directly into tissues also reduces drug dilution, metabolism and excretion, thereby significantly improving drug efficacy, while at the same time it minimizes systemic side-effects.

An important issue in targeted drug delivery is the accuracy of the navigational process used to direct the movement of the drug delivery device. Magnetic resonance imaging will likely play an increasingly important role in optimizing drug treatment of neurological disorders. One type of MR unit designed for image-guided therapy is arranged in a "double-donut" configuration, in which the imaging coil is split axially into two components. Imaging studies are performed with this system with the surgeon standing in the axial gap of the magnet and carrying out procedures on the patient. A second type of high-speed MR imaging system combines high-resolution MR imaging with conventional X-ray fluoroscopy and digital subtraction angiography (DSA) capability in a single hybrid unit. Both of these new generations of MR scanners provide frequently updated images of the anatomical structures of interest. This real-time imaging capability makes it possible to use high-speed MR imaging to direct the movement of catheters and other drug delivery vehicles to specific tissue locations, and thereby observe the effects of specific interventional procedures.

A prerequisite for MRI-guided drug delivery into the brain parenchyma, cerebral fluid compartments, or cerebral vasculature is the availability of suitable access devices. U.S. Pat. No. 5,571,089 to Crocker et al. and U.S. Pat. No. 5,514,092 to Forman et al. disclose endovascular drug delivery and dilatation drug delivery catheters which can simultaneously dilate and deliver medication to a vascular site of stenosis. U.S. Pat. No. 5,171,217 to March describes the delivery of several specific compounds through direct injection of microcapsules or microparticles using multiple-lumen catheters, such as disclosed by Wolinsky in U.S. Pat. No. 4,824,436. U.S. Pat. No. 5,580,575 to Unger et al. discloses a method of administering drugs using gas-filled liposomes comprising a therapeutic compound, and inducing the rupture of the liposomes with ultrasound energy. U.S. Pat. No. 5,017,566 to Bodor discloses redox chemical systems for brain-targeted drug delivery of various hormones, neurotransmitters, and drugs through the intact blood-brain barrier. U.S. Pat. No. 5,226,902 to Bae et al. and U.S. Pat. No. 4,973,304 to Graham et al. disclose drug delivery devices, in which biologically active materials present within a reversibly permeable hydrogel compartment can be delivered into tissues by various endogenous and exogenous stimuli. U.S. Pat. No. 5,167,625 to Jacobsen et al. discloses an implantable drug delivery system utilizing multiple drug compartments which are activated by an electrical circuit. U.S. Pat. No. 4,941,874 to Sandow et al. discloses a device for the injection of implants, including drug implants that may used in the treatment of diseases. U.S. Pat. Nos. 4,892,538, 4,892,538, 5,106,627, 5,487,739 and 5,607,418 to Aebischer et al. disclose implantable drug therapy systems for local delivery of drugs, cells and neurotransmitters into the brain, spinal cord, and other tissues using delivery devices with a semipermeable membrane disposed at the distal end. U.S. Pat. No. 5,120,322 to Davis et al. describes the process of coating the surface layer of a stent or shunt with lathyrogenic agent to inhibit scar formation during reparative tissue formation, thereby extending exposure to the drug agent. U.S. Pat. Nos. 4,807,620 to Strul and 5,087,256 to Taylor are examples of catheter-based devices which convert electromagnetic Rf energy to thermal energy. Technology practiced by STS Biopolymers (Henrietta, N.Y.) allows incorporation of pharmaceutical agents into thin surface coatings during or after product manufacture. The invention disclosed by STS Biopolymers allows for the drugs to diffuse out of the coating at a controlled rate, thereby maintaining therapeutic drug levels at the coating surface while minimizing systemic concentrations. The coating can incorporate natural or synthetic materials that act as antibiotics, anticancer agents, and antithrombotics, according to the issued patent. U.S. Pat. No. 5,573,668 to Grosh et al. discloses a microporous drug delivery membrane based on an extremely thin hydrophilic shell. U.S. Pat. No. 5,569,197 to Helmus et al. discloses a drug device guidewire formed as a hollow tube suitable for drug infusion in thrombolytic and other intraluminal procedures.

U.S. Pat. Nos. 6,026,316 and 6,061,587 (Kucharczyk et al.) advance the quality of delivery by enabling direct and even real-time observation of intraparenchymal drug delivery by non-invasive observational methods, even when delivery is itself invasive.

Published U.S. Patent Application No. 20030097116 (Putz, David A.) describes an improved assembly and method for accurately and safely delivering a drug to a selected intracranial site are disclosed. The assembly ensures delivery of the drug to the selected site by providing a barrier which prevents "backflow" or leakage of the drug. The assembly includes a guide catheter having an inflatable balloon which is able to seal or occlude the tract created by the insertion of the guide catheter into the brain. The guide catheter further includes a passageway which receives a delivery catheter through which the drug is administered to the selected site in the brain.

These advances within the field still allow for further advances in delivery methodologies that can improve or allow for alternative medical procedures for localized or distributed drug delivery within the brain. All references and Patents cited herein are incorporated herein by reference in their entirety.

SUMMARY OF THE INVENTION

A procedure or method allows for a unique positioning of materials and methods of drug delivery within or adjacent to tissues of a patient and especially within the skull and to regions of the brain. The new methods may be performed both for treatments and for evaluating the performance of a device or treatment for the delivery of materials in infusion delivery, perfusion delivery or catheter delivery of materials for diagnostic or treatment purposes. Observable material (e.g., material observable by invasive or non-invasive visual, MRI, PET, fluoroscopy, fiber optic or other methods) is delivered to a patient in a location within a patient where organs or tissue structures act in an active delivery mode (herein defined). The movement characteristics (e.g., direction of material movement, absorption rate, persistence or dwell time of the material, and movement rate) are observed in the active delivery position within the patient, and a delivery scheme is devised based upon the observed characteristics.

An active delivery mode is a new format of material delivery wherein a liquid to be administered (for diagnostic or treatment functionality) is provided, preferably in the form of a discrete mass, such as a bolus, directly between two opposed surfaces of a body element (e.g., especially the pia and the cortex) so that the discrete mass remains at least intact for a period sufficient to enable detection and observation. Where there is an existing fluid between layers, especially where that existing fluid is not rapidly moving (e.g., within blood vessels, flow of digestive fluids in tubes or vessels, etc.), the liquid delivery may be into that fluid, using the two enclosing surfaces as barriers against undesired movement of the delivered material, and assuring maximum local effect where desired. As greater mass of material is provided, the liquid material will be observed undergoing both flow between the layers and absorption into at least one of the opposed layers. The system may also be practiced with an implantable format, where either a passive (diffusion or timed release) or active (e.g., pump) delivery from an implanted element (e.g., at least a patch, tube, release pack, pump or microcatheter) being positioned between the opposed surfaces in the desired target location in the patient.

The technique can be used to determine appropriate delivery locations, delivery rates and delivery modes. The observational technique can thus be used to assist in specific treatment planning and assist in the improvement of device design by observing how catheter design variations affect the quality of material delivery. The format of an observational approach for defining proposed delivery methodologies such as those disclosed in U.S. Pat. No. 6,749,833 could also be practiced.

One method of delivery according to techniques and protocols described herein is the delivery between natural boundaries within a patient in a manner such that the material delivered persists in the region, zone, volume, space or location for sufficient time (without normal mass transfer events in the delivery site removing the material) for the treatment, diagnosis, observation or other procedure to take place while sufficient materials remains in the delivery site. Specially designed devices may assist in maintaining an appropriate or necessary concentration at the delivery site by preventing or educing back flow along the exterior sides of the delivery device.

BRIEF DESCRIPTION OF THE FIGURES

FIG. 19 shows four T1 weighted scans of the infusion of Gd-DTPA water solution.

FIG. 21 shows a third image of infusion of fluid into white matter producing changes that appear very similar to vasogenic edema.

FIG. 22 shows a graphic representation of distribution of high interstitial pressure adjacent material introduction.

FIG. 23 shows is an illustration of four sequential images of an infusion into a dog brain.

DETAILED DESCRIPTION OF THE INVENTION

Figure 1:
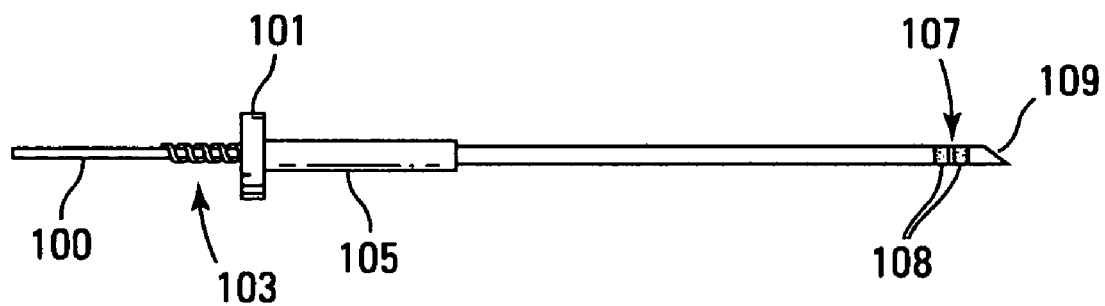
FIG. 1 shows a schematic of an assembled twin-stent catheter in pre-insertion mode.

The technology disclosed herein includes methods, devices, apparatus, protocols, and systems for the delivery of materials into a living patient. The material is delivered to a site where the material may persist for a time sufficient for allowing the observation, treatment, diagnosis, or the like to be performed without normal mass transfer events in the targeted sites removing the material or reducing the concentration of the material so rapidly or to such a significant degree as to prevent the effectiveness of the procedure.

It is to be noted that there are several limiting characteristics of all the catheters designed so far upon which improvements may still be made. In analyzing performance of catheters, the concepts of irreducible backflow, flow redirection and of active tissue should be considered. When a catheter or other surface is introduced into tissue, rupture of tissue often results. However, rupture and adverse effects of rupture can be (and are) minimized by smooth introduction and allowing the tissue to heal. Consider when an infusion of fluid commences (containing therapeutic material) into tissue by activation of a pump. The tissue is soft and deformable, easily undergoing shear strain—as when a doctor finds a lump in a breast, he or she is crudely estimating differences in shear modulus. This deformability of tissue results in there being a competition between water pushing the tissue back so as to clear a channel along the outer surface of the catheter for easy flow versus the more difficult flow into the tissue, which is a porous medium filled with obstacles (cells) around which the fluid flows. (Water enters into and out of cells by the slower process of diffusion.) The resistance to deformation is measured, to a first approximation, by the shear modulus G, while that to flow into the tissue is measured by the fluid permeability k as well as the viscosity of the fluid. G and k are intrinsic properties of the tissue, and have nothing to do with the skill of the surgeon inserting the catheter. Irreducible backflow is defined as the length (or other suitable dimension describing the flow along the surface of the catheter or device) of the fluid channel along the outer surface of the catheter that depends only on G, k and, of course, the geometry and parameters of the insertion (catheter dimensions, flow rate, viscosity). For usual cylindrical catheters of outer diameter of 1 millimeter at some clinical flow rates of less than a half milliliter per hour, these lengths are up to 3 centimeters. This is an intrinsic limitation of current catheters, that the infusion into tissue spreads not just from or predominantly from the tip or port of the catheter (of radius less than ½ mm.), but rather from an extended surface of linear dimension 2-3 centimeters, and the infusion into tissue is variable according to the properties of the tissue adjacent to the catheter.

The second concept considered is that of flow redirection. The concept of "inertia" even in its customary non-technical meaning allows us to guess (and this assumption is supported by deeper understanding of fluid flow in deformable porous media) that if backflow is redirected to another very distinct direction (ideally involving an abrupt change of direction), the subsequent flow will not easily return to the original direction of backflow. This is a concept that may be exploited in this present invention. The pertinent fact is that once a sufficiently abrupt flow redirection is effected for a sufficient distance, the redirected streamlines will tend to persist and not return to their original configuration without further intervention. This effect may be reinforced by having tight seals on either side of an interface between two distinct layers, and also by the creation of channels due to the active response of tissue to pressure, another concept that is now explained.

The third concept, which points to a second feature of the present technology is what is termed active tissue. The tissue, as already mentioned, is highly deformable, at least under shear. In fact, owing to the interlacing of blood vessels and other highly deformable reservoirs, it is also effectively quite compressible, even though its constituents, e.g. cells, are not. The net result is that when subjected to pressure-driven fluid flow, the tissue deforms, sometimes quite dramatically, sometimes more subtly, but often reliably enough to take advantage of this and not merely regard it as a nuisance. Active tissue exploitation is a feature of the present technology and may work in more than one way, resulting in more than one embodiment. We describe several embodiments below.

A fourth feature of the present technology is the exploitation of irreducible backflow itself to spread infusate over regions otherwise not easily penetrable.

One method of delivery according to techniques and protocols described herein is the delivery between at least two distinct and different natural boundaries within a patient in a manner such that the material delivered persists in the region, zone, volume, space or location for sufficient time (without normal mass transfer events in the delivery site removing the material) for the treatment, diagnosis, observation or other procedure to take place while sufficient materials remains in the delivery site. Natural boundaries include surfaces of tissues, organs, bones, ligaments, cartilage, and the like. By distinct and different it is meant that the natural boundaries may not necessarily be opposed surfaces of essentially the same material within a single component of an organ. For example, the space defined within a blood vessel has the essentially identical blood vessel walls opposing each other (in an essentially continuous manner) because of the structure of the vessel. Similarly the space within sacs in the lungs, within ducts, in the volume of the stomach, within the cochlea, between muscles, and the like are not distinct and different. The opposed tissue surfaces of the pia and cortex are non-limiting examples of distinct and different opposed surfaces. As noted above, the delivery may be through an implanted format, where there is active or passive delivery from an implanted system, with the physical delivery occurring between the opposed tissue surfaces. For infusions into deep brain structures, where the catheter is inserted 20 mm or more into the brain, this may pose relatively little problem. However, for infusions into the cortical structures, which are typically thin layers near the surface of the brain, this could impose a stringent limit on the utility of the technique and affords a basis for indwelling device delivery.

It is also desirable that the opposed surfaces have natural fluid reservoirs or mass between the distinct and different layers. These reservoirs or masses should be mass transfer stable. That is, the materials within a given local volume, especially the targeted volume, should not be essentially 100% (e.g., no more than 80% and even no more than 70%) replaced within a 5 minute period (preferably less than 3, more preferably less than 2 minute, less than 1 minute, and less than 30 second) under normal environmental and functional events at that site. For example, blood vessels within a moderate length of time (e.g., less than 30 seconds) will replace essentially all blood within a moderate length of an artery or vein in a relatively short time. Ducts during normally active periods may replace fluids by mass transfer in longer time frames, but still within the 5 minute period identified above. Material is replaced over time in these regions, but usually by transparenchymal migration, perfusion, permeation and discharge, not by regular and relatively high percentage volume mass flow.

Specially designed devices may assist in maintaining an appropriate or necessary concentration at the delivery site by preventing or reducing back flow along the exterior sides of the delivery device. Structures that tend to block or seal edges of the openings at the site of physical introduction of the delivery device, and especially around the sides or edges of the point of penetration of tissue by the delivery device are very desirable as this enhances the retention of the material at the delivery site and reduces unnatural (from the penetration of tissue) flow paths from the targeted site. Such blocking or sealing structure may include inflatable surface functionality on the tube, gaskets, parasols, stents, tensioning surfaces that can cover or secure a region extending from the device surface over a sufficient area of the penetrated surface to assure an improved seal at the site of penetration. For example, the catheter may be a coaxial (two concentric lumens) catheter where the innermost catheter delivers the material and the outermost catheter wall is flexible or elastic and carries a fluid which may be pressurized to firm the seal between the catheter and the tissue, and even slightly bulge above and/or below the penetration site to prevent leakage.

Various aspects of the disclosed technology may be generally described as including a method for the provisioning and positioning of a flowable material into a region of a patient comprising: identifying a region of a patient to be viewed or treated; identifying a region wherein the region forms a potential volume between two opposed different and distinct surfaces; penetrating at least one of the two opposed different and distinct surfaces with a material delivery device; and providing material from the material delivery device into the potential volume to create a volume containing at least delivered material. The method may have the volume as a mass transfer stable in that less than 80% by volume of delivered material is removed from the created volume by natural biological activity in less than 5 minutes. The material delivery device may form an at least partial seal around a puncture formed by penetration of only one of the at least two opposed different and distinct surfaces. The seal may be formed to cover a surface area extending circumferentially away from and around a diameter of the material delivery device. The seal may be formed on both sides of the puncture relative to the opposed surface penetrated, or the seal may be formed on only one side of the puncture relative to the opposed surface penetrated. A structure forming the seal may be distended, distorted, expanded, bent, flattened and/or inflated to assist in sealing the puncture. For example, a structure forming the seal may be flexible and distort to apply pressure over the puncture. The two opposed surfaces may comprise the pia and the cortex.

A medical device for delivering material through tissue into a defined area of a patient may, by way of non-limiting examples, comprise: a material delivery element through which the material may flow out of a delivery end; the delivery end having an opening that can be inserted through a surface of the tissue; and a sealing system proximal to the delivery end that can extend away from the material delivery element along the surface of the tissue and apply pressure to the tissue after the material delivery element has been inserted through the surface of the tissue. The material delivery device may be selected from the group consisting of a catheter and needle. The sealing system may comprise at least two structural elements that are displaced from each other along the delivery end of the material delivery device. The two structural elements may be disposed at positions on opposite internal and external sides of a puncture in the surface of the tissue. The sealing system may be inflatable. There may be a second seal formed against at least one surface in addition to the punctured surface, as where the punctured surface may be the pia and the second surface may be the dura.

The sealing system may comprise at least two components lying along a long axis of the material delivery device and within dimensions of a largest radius of the delivery end of the material delivery device in an at-rest position. The at least two components of the sealing system may have their shape and size altered to assist in forming a seal. A non-limiting example of this is where each of the at least two components has an initially tubular form and their exterior surfaces are coplanar with the material delivery device outer surfaces and the stents are essentially identical. Sealing procedures may cause the two components to alter their size and shape and consequently distort approximately equally. There may be a washer or armature barrier mounted between the at least two components concentric to the material delivery device.

The stents may each consist of a flexible tube, and during or after initial deployment, the final disposition of the stents is achieved by reducing the longitudinal space available to them where they are mounted on the catheter needle. The deployment of the tube stents may be achieved by longitudinal compression achieved by movement of the catheter needle within the main body or outer casing of the catheter. The position of the catheter body relevant to the distal tip and mass of the catheter needle may be adjusted automatically as the mechanism deploying the stents is activated, the two movements being linked.

Examples of other sealing devices include sliding gaskets that may be moved along the exterior surface of the delivery device to abut the penetration site, parasols that may be deployed at the penetration site, and a design referred to herein and described in greater detail elsewhere as a twin-stent design.

Figure 16:
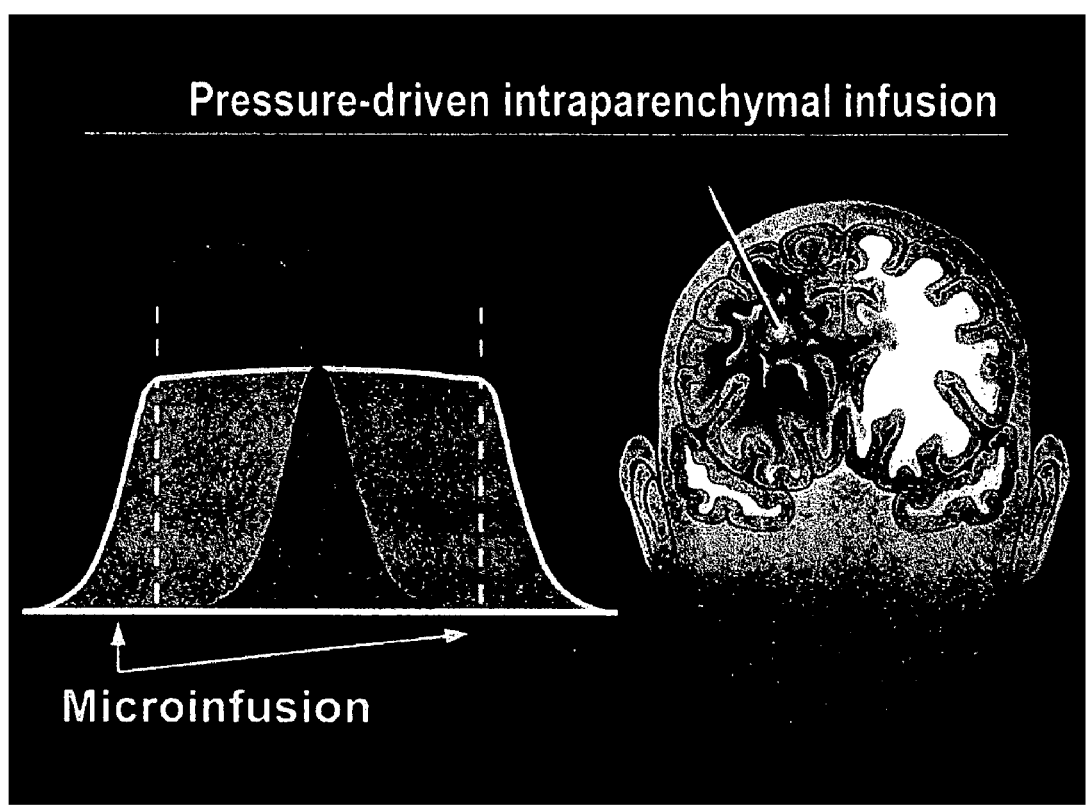
FIG. 16 shows a graphic representation of pressure-driven intraparenchymal infusion.

For many years, researchers have attempted to deliver drugs to the brain using localized infusions, known as "Convection-Enhanced Delivery" (CED). Convection-enhanced delivery (CED) is an innovative drug delivery technique that promises to enhance the spatial distribution of therapeutic agents throughout brain parenchyma. CED establishes a bulk flow interstitial current through direct intracerebral infusion that has the potential to uniformly distribute even large molecules over much greater distances throughout the brain, as the figure below illustrates:

What is shown in the FIG. 16 (which is not to scale) is a comparison of the rather limited spread one could expect from the diffusion of a macromolecule, compared to where it can be carried by fluid flow. In fact for large molecules of the size of a globular protein of weight 50,000 Daltons and above, the diffusive spread will be often less than a millimeter in a day, not allowing for metabolic and other loss mechanisms. The flow of a fluid co-injected with a drug can however carry such molecules far farther, and in certain idealized scenarios fill the intervening region with a full concentration of drug per unit of available volume. Diffusive spread results in exponentially decreasing concentrations away from a source.

However, the success of these attempts has to date been limited, since the localized delivery was lacking appropriate planning, guidance and infusion technologies. Currently, intra-parenchymally injected agents are not monitored to determine their spatial disposition in tissue. Recently, following CED of novel therapeutic agents in humans with malignant gliomas, the inventor has been able to obtain images that document the spatial distribution of large molecules in several patients with brain tumors. These data demonstrate that CED is capable of significantly enhancing the spatial distribution of drugs beyond that which would be obtained by diffusion alone. However, in internal studies, the measured spatial distributions varied significantly from patient to patient in an apparently unpredictable fashion. Thus, notwithstanding improvements in drug distributions, the actual geometry of the spatial distribution obtained in a given patient frequently failed to reach the intended regions of interest and left regions of likely tumor recurrence unaddressed. This variability clearly constrains the potential of the therapeutic agent being delivered.

In most procedures for intraparenchymal infusion or injection, the delivery device is stereotactically guided to its intracranial target through a burr hole. For slow infusion processes, (typically in humans of rather less than 0.3 milliliters per hour) the catheter might be left indwelling for several days. Conventional MR/CT imaging studies are typically used pre-operatively to estimate the optimal insertion trajectory. However, the final operative details of the implantation procedure are usually specific to the design of the delivery device, the rate at which the infusion or injection is to occur, and the number of devices that must be inserted and/or passes that must be made to obtain adequate therapeutic coverage of the targeted volume. Infusion methodologies for both framed and frameless stereotaxis have been developed, with forms of the latter optimized for use in the interventional MR setting.

Flow Containment

Problems that can potentially occur during any kind of intraparenchymal infusion or direct injection approach include backflow along the catheter or cannula insertion track, suction-displacement or reflux of the infused agent or injected cells along the withdrawal track during removal of the catheter or cannula, and cyst formation and other neurosurgical complications. Backflow can result in spread of the agent into regions of the brain where it is not intended and, possibly, in diminution of the dose otherwise needed within the target tissues. The same holds for reflux during withdrawal. The problem could be particularly acute in cortical infusions, where backflow of the agent along the insertion track and into the subarachnoid space could occur, with subsequent widespread distribution of the agent by the circulating cerebrospinal fluid. The inventor is developing a model of the mechanics of the backflow process, and in it the backflow distance (for a fixed rate of fluid delivery through the catheter) varies as the four-fifths power of the catheter radius. In testing this model versus observations of infusions predicted backflow distances on the order of 20 mm were found to indeed occur. For infusions into deep brain structures, where the catheter is inserted 20 mm or more into the brain, this may pose relatively little problem. However, for infusions into the cortical structures, which are typically thin layers near the surface of the brain, this could impose a stringent limit on the utility of the technique unless a means is found not only to prevent this backflow but then to spread the infusion into the thin cortical layer without being sumped by the underlying white matter. The catheter designs conceived and tested during one phase of the inventor's initial efforts achieved this goal. This problem will be particularly acute in animal brains which are much smaller. Currently, for infusions into humans, the best navigations systems offer the following guidelines, which were suggested by the inventor.

Figure 17:
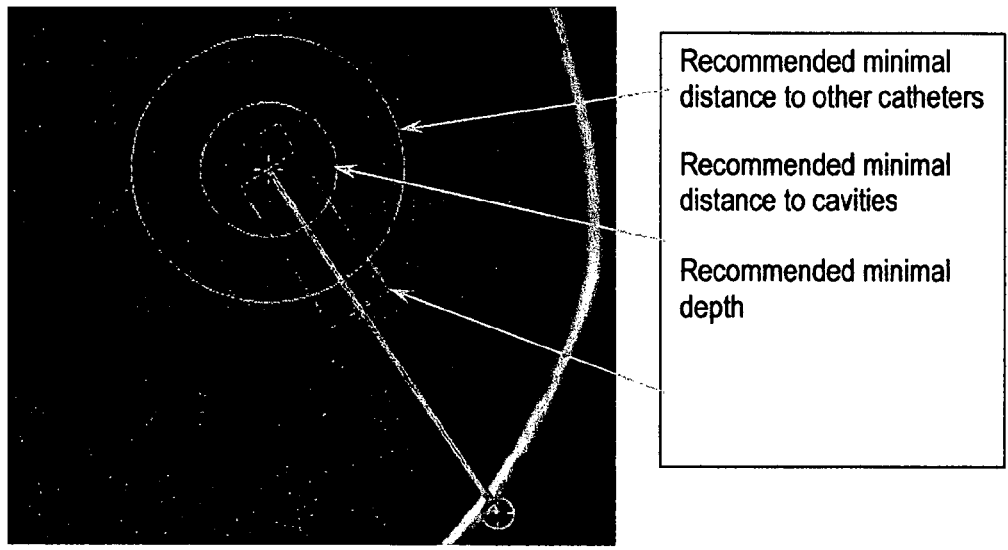
FIG. 17 is an overlay of recommended distances used during infusion delivery by catheter.

Two Guidelines illustrated in FIG. 17 can be separately or together be displayed by selecting one or both of the guidelines. Currently, for infusions into humans, the inventor offers the following guidelines:

Depth Line

This could be effected by a cylinder positioned along a catheter trajectory representing a recommended zone within which the catheter should not cross any pial surfaces. The material to be dispensed from the implanted system may also be represented as a sphere around the catheter tip representing a recommended distance to fluid filled cavities.

Distance Line

The depth line of delivery may also be represented on a map of the target area by a sphere of 2 cm diameter around the catheter tip representing the recommended minimal distance between catheters.

There are numerous types of implantable patches that can be inserted into patients that are commercially available, but none of these have been used to provide the administration or delivery of medically applicable materials between the opposed surfaces to control the rate and location of delivery. Is possible for a patch type material to be delivered, as by putting the active ingredients in a mass that will persist for a period of time that is desired, and then harmlessly dissolve. The mass could be as rapid dissolving and harmless as mannitol, rabbitol or other sugar-type material, or could be more persistent, yet harmless with natural polymers such as gelatin or gums and resins (amylase). It is possible to use soluble synthetic polymers (such as polyvinyl alcohol), but because of the location of the material, carrier media should be carefully considered for their toxicity and undesirable level of persistence.

The outer circle in FIG. 17 shows the Distance Line and the inner circle in combination with the cylinder along the trajectory the Depth line. The following described graphics illustrate in more detail the guidelines. The basic point from all of these Figures is that such restrictions are completely out of the question for small animal brains. In the first figure below 18a, we show an acceptable placement since the backflow distance is less than the distance to any dangerous fluid reservoir.

On the other hand, the following is not recommended since there is danger of backflow into the sub-arachnoid space, thereby providing a path of essentially zero resistance to the fluid flow which will therefore not suffuse the tissue surrounding the catheter tip. The two scenarios below indicate two ways this might happen; one in which the insertion is unhappily along a sulcus, and the other in which it is transverse to one. These features are shown in FIGS. 18A, 18B, 18C and 18D.

Figure 18A:
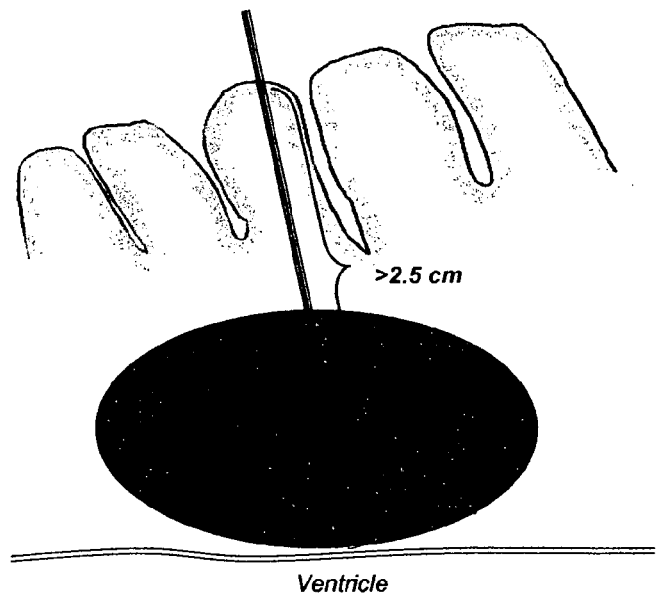
FIG. 18A shows a guideline for catheter insertion.
Figure 18B:
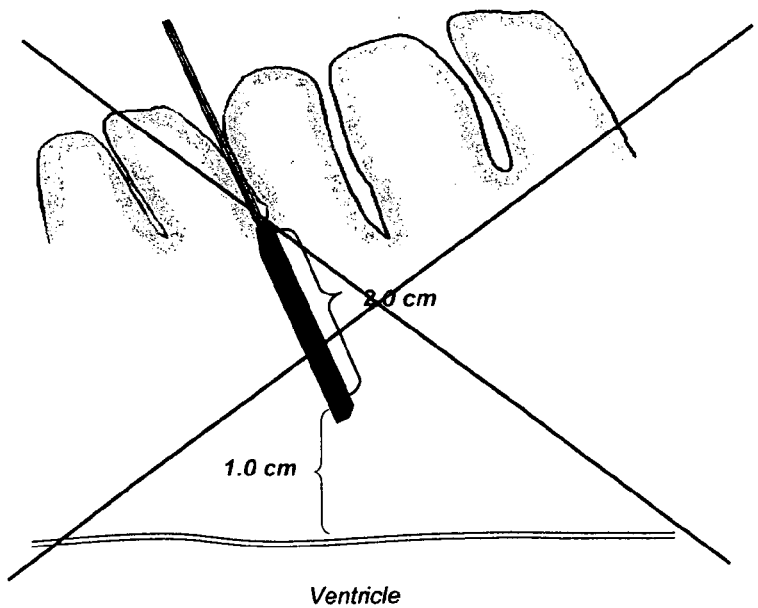
FIG. 18B shows a guideline for catheter insertion.
Figure 18C:
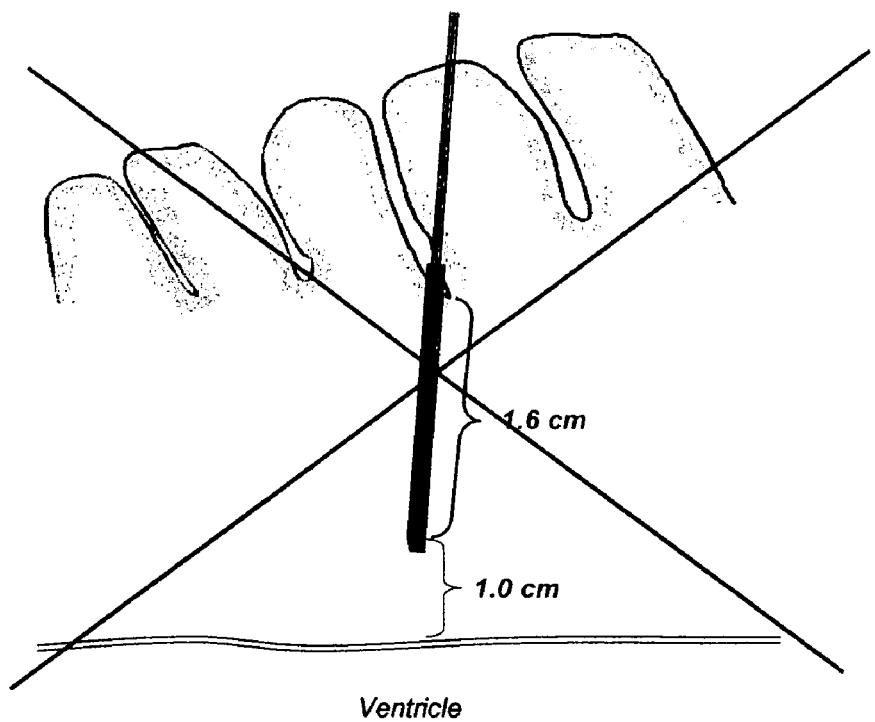
FIG. 18C shows a guideline for catheter insertion.
Figure 18D:
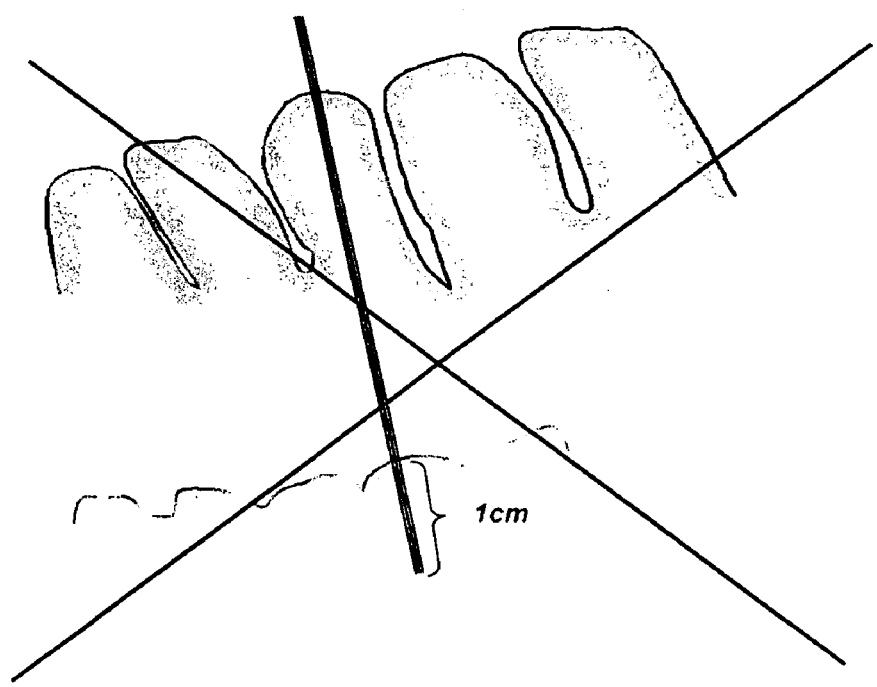
FIG. 18D shows a guideline for catheter insertion.
Figure 18E:
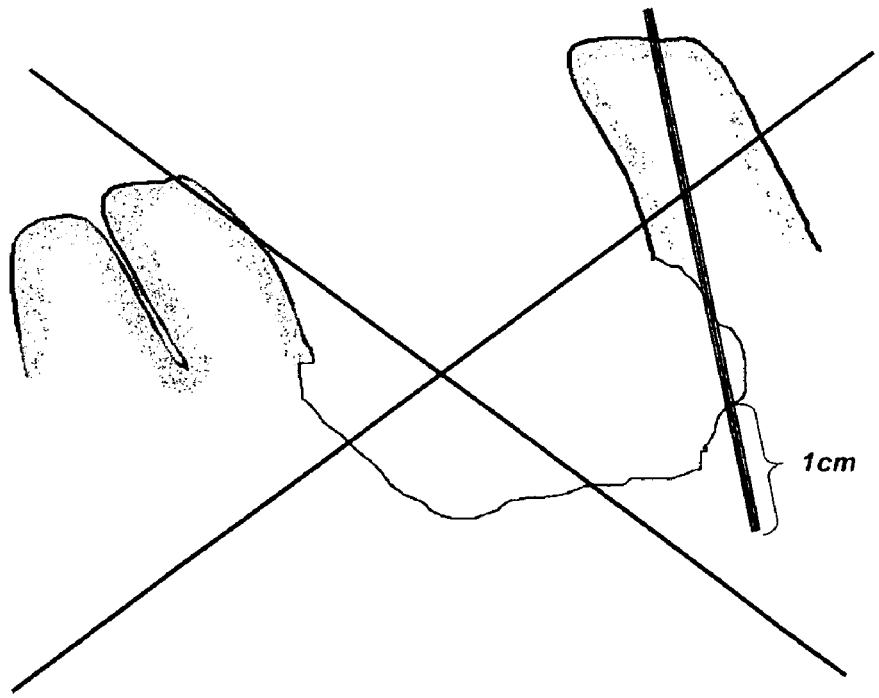
FIG. 18E shows a guideline for catheter insertion.

The next FIG. 18B shows a poor placement that is the result of the following process. The catheter was inserted too far and encountered a fluid reservoir (e.g., ventricle, resection cavity). It was then withdrawn back into the tissue proper. However, this will leave an unhealed track and any infusion is likely to follow it into the reservoir. Equally, traversing an "internal" sulcus like the Sylvian fissure will also compromise an infusion, as shown in FIG. 18E.

Figure 18F:
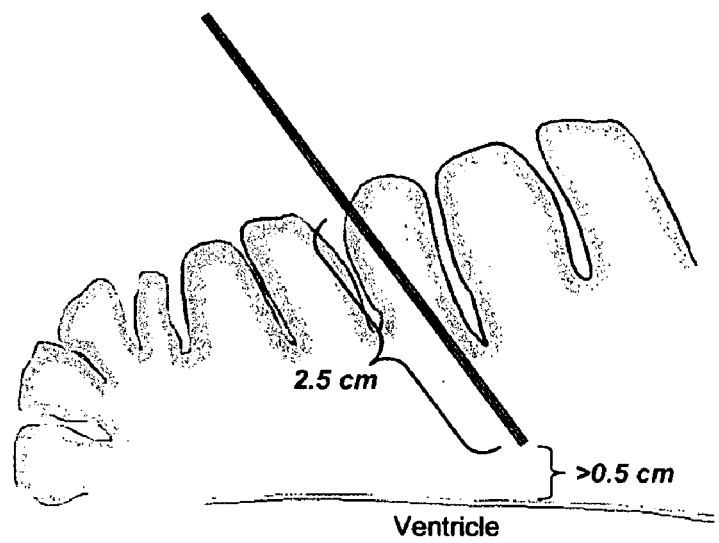
FIG. 18F shows a guideline for catheter insertion.
Figure 18G:
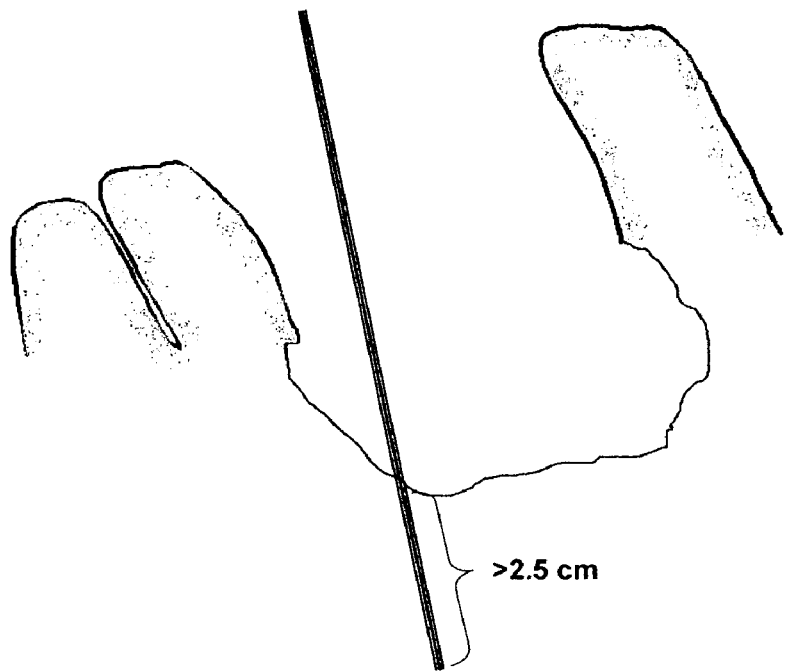
FIG. 18G shows a guideline for catheter insertion.
Figure 18H:
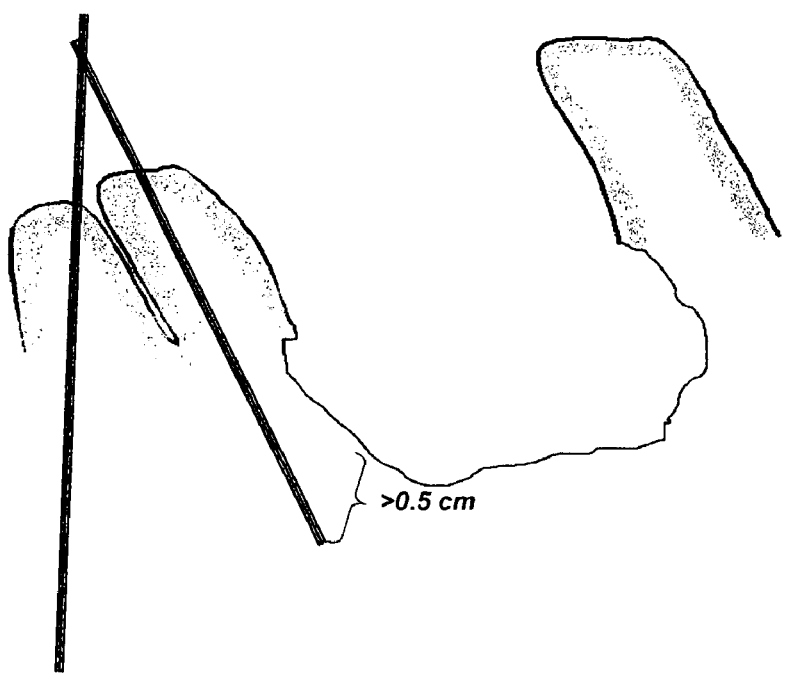
FIG. 18H shows a guideline for catheter insertion.

Traversing a resection or other cavity with a placement that is likely to result in backflow reaching the cavity also obviously compromises the infusion in FIG. 18F. However, both theory and observation suggest that flow forward of the catheter tip is essentially negligible, and therefore, the following graphics indicate acceptable catheter positioning. It should, however, be mentioned that the low pressure in fluid-filled cavities also means that such infusions will not spread as far in tissue as they otherwise might. However, the infusions will not be totally compromised, as they would in cases of leaks into the sub-arachnoid space, as shown in FIG. 18G. Thus while the backflow distance to a cavity must allow for a safety margin as shown in FIG. 18G, a much smaller distance away from the catheter track will do, as shown in FIG. 18H.

The FIG. 19 illustrates the leakage of infusate into the subarachnoid space via backflow up the catheter. A 0.85 mm diameter catheter was inserted through a burr hole into in-vivo pig brain to a depth of 14 mm from the cortical surface. 1:200 Gd-DTPA:water solution was infused at 5 microliters per minute. 3D MR imaging (3D-FSPGR, TR=7.8 ms, TE=3.2 ms, 256×256 matrix, FoV=20 cm, 1 mm slice thickness, 60 slices, 2 NEX, flip angle 15°) was performed to analyze the dispersion of the Gadolinium marker. Images taken after 32 minutes of infusion show evidence that the infusate has mostly leaked into the subarachnoid space. This distributes material widely along the contours of the cortex, while little distribution into the white matter was recorded.

FIG. 19 shows infusion of 1:200 Gd-DTPA:water solution with four T1-weighted 3D SPGR slices, at a 3 mm separation. The infusion catheter is visible in the first slice (left). Subsequent slices reveal leakage and spread of the infusate into the subarachnoid space.

So far, the disclosure has focused on situations where the backflow or flow into fluid filled cavities would almost totally compromise the infusion. There is, however, another path which very significantly affects infusions, and which needs to be considered. This is the increased fluid permeability offered by the white matter tracts, and which dramatically increases in edematous brain. However, just infusion of fluid into white matter produces changes that appear very similar to vasogenic edema. When infusing into white matter that does not already contain edema, edema appears around the catheter (see FIGS. 20a, 20b and 21). Relatively little edema is seen near the tumor recurrence which is below the resection cavity before infusion (FIG. 20b). After 44 hours of infusion, a large and intense edema surrounds the catheter (FIG. 20b. FIG. 21 shows the distribution of SPECT marker roughly matching the area of edema. The extent of the edema appears to match the extent of the infused fluid closely, according to infused gadolinium and SPECT markers. The level of the infusion-related edema for a 4.5 µL/min infusion is often greater than that observed of tumor-induced vasogenic edema. In T2-weighted images, the T2 levels near the infusion reach values very near that of fluid-filled cavities and ventricles. The infusate itself may have a higher T2 than that of CSF, so it is difficult to make a quantitative assessment from the T2 weighted values as to whether the infusion-induced edema has a water fraction higher than that of the average vasogenic edema. These are displayed in FIGS. 20a, 20b and 21.

The upshot of all this discussion is particularly relevant for:
Cortical Infusions Direct targeting of the cortical grey matter for sub-pial infusion is complicated by the tendency of the infusate to backflow along the catheter shaft for several centimeters, depending upon flow rate, catheter radius, and properties of the tissue. In cases where the catheter tip is placed at a depth less than the backflow distance, the infusate tends to follow the low-resistance path out through the pia and into the sub-arachnoid space. The fluid distributes widely through the subarachnoid, but for most infused compounds, the pia acts as a barrier preventing the compound from entering the cortex. White matter infusions can sidestep this problem by placing the catheter deep within tissue, far from the brain surface, an option not available for cortical infusion.

Figure 20A:
FIG. 20A shows a first image of infusion of fluid into white matter producing changes that appear very similar to vasogenic edema.
Figure 20B:
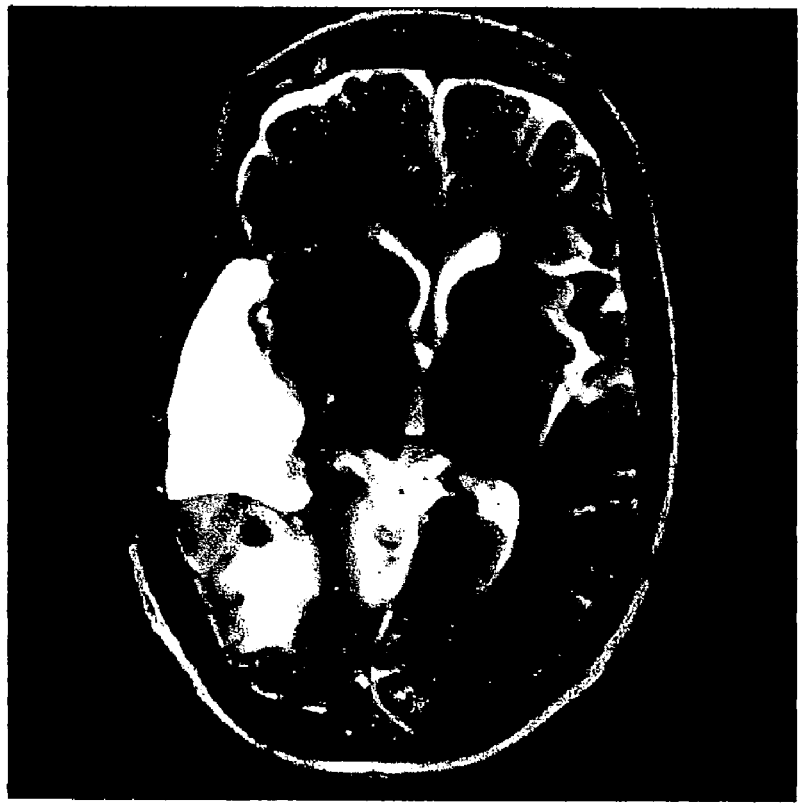
FIG. 20B shows a second image of infusion of fluid into white matter producing changes that appear very similar to vasogenic edema.

The FIGS. 20a, b and 21 illustrate this. A standard catheter when Infusions into tumors present their own special problems. Active tumors present a variety of additional barriers to drug delivery
high interstitial tumor pressure (as shown in FIG. 22)
decreased vascular surface area, heterogeneous distribution
increased intra-capillary distance
peritumoral edema, disrupted blood brain barrier This is illustrated in the four images of FIG. 23. The magnetic resonance images taken of an infusion into a dog show rather clearly the barrier presented by an active tumor.

The above described features of technology will be enhanced by a reading of the examples. Below are additional features and structures useful within the practice of the described technology.
A Twin-Stent Cortical Catheter It is believed that, being a generally impermeable or at least weakly permeable barrier, the pia offers a membrane that can be used to hold materials, especially materials with a molecular weight above 400, above 500, above 1000 and the like, and especially markers and medication against the cortical surface using an appropriate method of delivery described herein, especially using specifically designed catheter elements. The structure of the catheter element can be observed and enhanced under observation, here by direct (including MR, X-ray, fluoroscopy, CT etc.) visual observation.
Control Experiment:

When a conventional catheter needle is used to introduce liquid through the pia the usual outcome is that a significant amount, if not most of the liquid, taking the easiest path, flows back along the sides of the needle to the point of entry through the pia, from where it escapes helped by the flow of CSF.

The extent to which the introduced liquid leaks out through the hole created in the pia by the catheter is observable by the discoloration of a white tissue that has been laid against the external surface of the pia. Alternatively, during an evaluative process of various catheter needle design, a marker, dye or pigment may be used and the material observed directly (e.g., with optical fibers) or by medical visualization techniques (e.g., MR, ultrasound, fluoroscopy, PET, CT, etc.) to see the leakage of the material that is in visible contrast with its surroundings. By observing these results, delivery characteristics of either a general nature (developing general procedural formats), a device specific nature (for different catheter designs and sealing system designs) or a patient specific nature (developing patient specific procedural formats) can be determined. The format for a specific patient can be performed well in advance of the actual treatment, or can be performed immediately preceding the treatment, using an inert observable medium for observation. A plan or strategy of treatment can be developed from the observed characteristics.

The reasoning upon which the novel treatment process relies (using natural boundaries between opposed surfaces in the body, excluding opposing vessel walls or duct walls as considered opposed surfaces) upon the idea that if the liquid can be prevented from escaping through the hole in the first opposed surface (e.g., the pia) through which the material is delivered so that any backflow tendency could be exploited by using it to gather a bolus of liquid just below the (opposed surface (e.g., pia) at the point of entry, from where it would then spread out (because of surface tension or pressure applied by gravity or elasticity of the opposed surfaces) between the pia membrane and the cortical surface and be absorbed by the other opposed surface (e.g., the cortex), which would be an intended purpose of this catheter design.

One observation of this example is to demonstrate the viability of observing the introduction of medication between the pia mater and the exterior cortical surface in order that it can then be observed as it is absorbed by the cortex and as it move between the opposed surfaces in a manner that can be controlled and/or predicted. Different sealing designs are also considered and used.

One method adopted was to construct a model of a simple twin-stent catheter design of which the principal novel feature was a pair of stents lying in the main axis of the catheter needle very near the distal tip. Each stent consists of a short length of silicon or polymer tube mounted around the catheter core between the casing and the enlarged needle tip. (For a production model the same result might be achieved in slightly different ways but the purpose of this simply-constructed model was to test the principle rather than to finalise mechanical details of the design). The stents are used so that one stent is positioned interior of the puncture and the other stent is positioned exterior of the puncture. The two stents act in concert to apply pressure around the circumference of the puncture from both sides of the pia to form a seal round the periphery of the puncture. This seals the puncture against back leakage.

Compression of the twin stents by means of the reduction of the gap between the two stents on opposite sides of the puncture causes each stent to displace outwards, consequently adopting the form of a disc instead of a cylinder. If both stents or even a single flexible stent is on one side of the puncture, sufficient pressure against a flexible, elastic stent at an end of the stent distal from the puncture can assist in causing the end of the stent proximal to the puncture to press on the circumference of the puncture and even to distend outwardly in the middle of the stent to form a doughnut-like shape and assist in sealing the puncture further. A narrow washer (of the same diameter as the casing and tip) may be used to separate the two stents causes them to distort identically.

The needle tip is preferably placed within the outer casing and is partially withdrawn. The spring stiffness (resilience) then pushes and expands the rubber or rubber-like stents which in turn expand outwardly. By placing a washer at the interface where the seal is desired, the stents when expanded do so equally and form the seal.

The technology described herein allows for a method of providing and positioning a flowable material into a region of a patient. A flowable material is generally a liquid solution, but may also be a suspension, dispersion or emulsion that exhibits flowable characteristics similar to those of a liquid. The method may comprise identifying a region of a patient to be viewed or treated; identifying a shaped volume between two distinct surfaces within the region; identifying a flow redirection mechanism to confine infusate within the shaped volume; and providing material from a material delivery device into the shaped volume to create a delivery volume between the two distinct surfaces containing at least delivered material. The method may use an active response of the tissue to flow of infusate that is considered in restricting the flow to within said volume. The method may be practiced where a path of movement of the delivered material is confined or directed in flow by exploitation of backflow and redirection. The backflow and redirection (as described herein) may be created by pneumatic and tensile forces provided by at least one of the delivered material, tensile forces of the two distinct surfaces, shape change of the delivery device and volume change of the delivery device. FIG. 1 shows a schematic of an assembled twin-stent catheter 100 in pre-insertion mode. The catheter 100 elements 101 which is a position stabilizing element or plate; 103 which is a screw threading or other mechanical advancing system; 105 which is a guidance support element; 108 which are a pair of stents that are separated by spacer 107 and the insertion tip 109 of the catheter 100.

Figure 2:
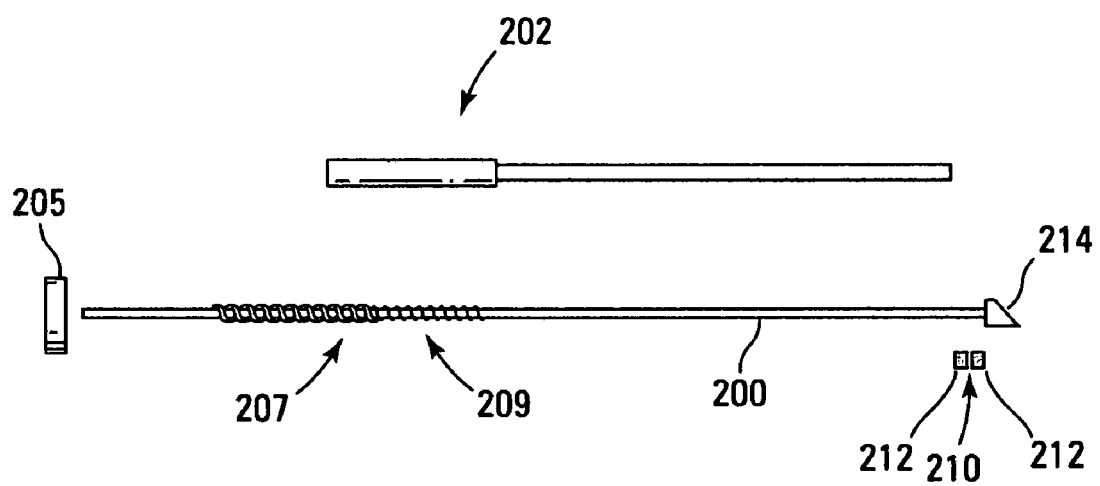
FIG. 2 shows the component parts of a twin-stent catheter.

FIG. 2 shows the component parts of a twin-stent catheter 200 comprising the guidance support element 202, the position stabilizing element 205, a pair of threaded advancing systems 207 208, the catheter tip 214, the two stents 212 and the spacer 210 between the stents 212.

Figure 3:
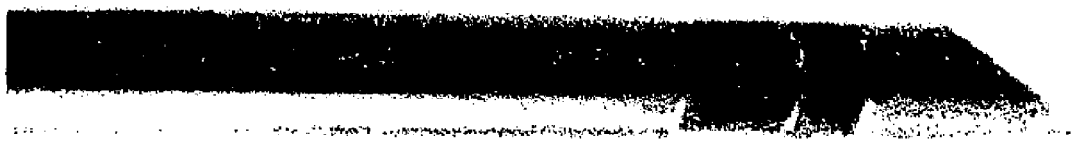
FIG. 3 shows the distal tip of the twin-stent catheter in pre-insertion mode.

FIG. 3 shows the distal tip 304 of the twin-stent catheter 300 in pre-insertion mode. The barrel 306 extends to the pointed end 314 of the catheter 300 where the twin or dual stents 312 are separated by the spacer 310, which may also operate to close or diminish any penetration hole by being expansible.

Figure 4:
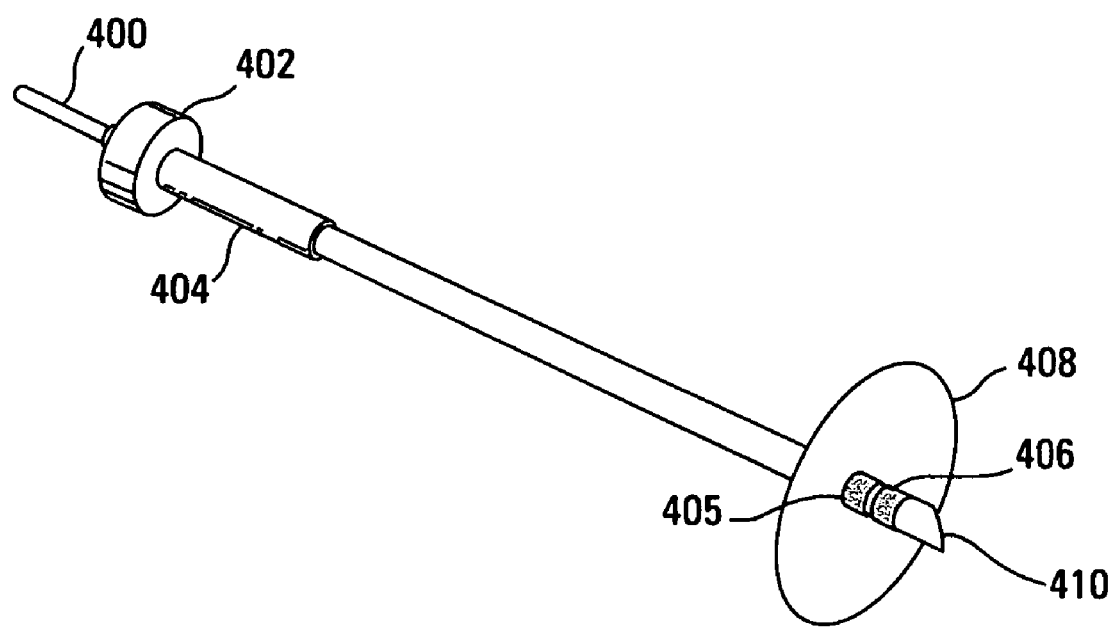
FIG. 4 shows a schematic of the twin-stent catheter in initial position piercing the pia.
Figure 5:
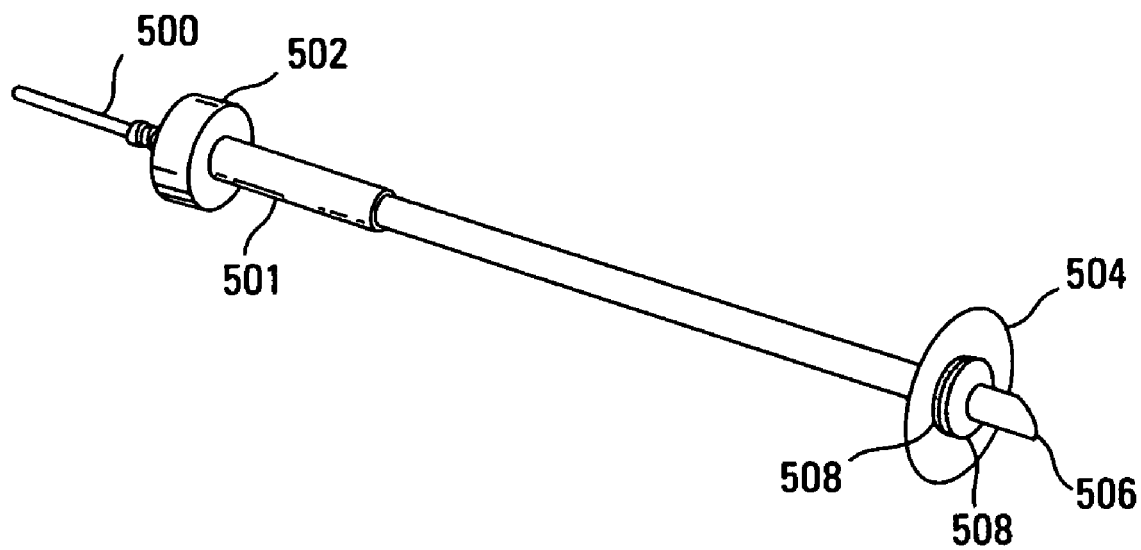
FIG. 5 shows a drawing of the contracted twin-stent catheter gripping the pia.

FIG. 4 shows a schematic of the twin-stent catheter 400 in initial position piercing the pia 408. The forward stent 406 is shown along with the pointed tip 410 on the distal side of the pia 408. The proximal stent 405 is shown on the proximal side of the pia 408 along with the guidance support element 404 and the stabilizing support element 402. FIG. 5 shows a drawing of the contracted twin-stent catheter 500 gripping the pia 504. The two stents 508 are inflated to stabilize the catheter and seal the hole (not shown) from the puncture by the pointed tip 506. The guidance support element 501 and the stabilizing support element 502.

The various twin/dual stent catheters may be held firmly in this position by the locating jig (not shown or described) whereby the adjuster screw is then tightened so that the two stents distort to the extent that they firmly grip the pia between them, thus sealing the hole made in it by the entry of the catheter. In the actual test model illustrated, a threaded nut-and-screw arrangement allows for the manual adjustment of the compression of the stents and therefore the degree of distortion of the pair of stents. A spring contained within the case may be used to return the stents to their original at-rest cylindrical form when the adjusting screw is slacked off.

The stents distort because the space available to them is reduced. It follows that the distance between the washer located between the two stents and the distal tip of the catheter needle is also reduced as the distortion is increased. The position of the casing of the catheter therefore needs to be slightly adjusted to maintain the washer at the level of the pia so that the stents precisely grip the pia between them as they complete their distortion.

The technology described herein allows for a method of providing and positioning a flowable material into a region of a patient. A flowable material is generally a liquid solution, but may also be a suspension, dispersion or emulsion that exhibits flowable characteristics similar to those of a liquid. The method may comprise identifying a region of a patient to be viewed or treated; identifying a shaped volume between two distinct surfaces within the region; identifying a flow redirection mechanism to confine infusate within the shaped volume; and providing material from a material delivery device into the shaped volume to create a delivery volume between the two distinct surfaces containing at least delivered material. The method may use an active response of the tissue to flow of infusate that is considered in restricting the flow to within said volume. The method may be practiced where a path of movement of the delivered material is confined or directed in flow by exploitation of backflow and redirection. The backflow and redirection (as described herein) may be created by pneumatic and tensile forces provided by at least one of the delivered material, tensile forces of the two distinct surfaces, shape change of the delivery device and volume change of the delivery device.

FIG. 4 shows the distal tip of the catheter with the twin stents contracted to form the doughnut-like gasket elements that can seal the hole in the pia from two sides of the puncture.

FIG. 5 actually shows the contracted external stent from a twin stent catheter pair gripping the pia, creating a seal around the puncture. As the stent can spread laterally away from the catheter to cover an area extending around the complete periphery of the puncture, an effective seal can be provided. If there were a pneumatic connection to the stent or gasket-like element, and if the material in the construction of this component were elastic, pneumatic pressure might be used to provide pressure and extend the area of coverage of the device component. Rather than using twin stents, a lip, grip, tongue or other structural component may be used to keep the distal side of the stent or gasket restricted from sliding along the catheter while the expanding stent or gasket applies greater pressure against the pia puncture.

In the tests, the position of the body of the model was adjusted by hand. However, because the extent of this movement will be the same each time, a production model would likely incorporate a device to change the position of the catheter casing in direct proportion to the degree of compression and the consequent extent of distortion of the stents. Observation of the variations in this design may be made according to the practices of the process described herein, and the effects of variations in design observed in the performance of the delivery process under real time or images observation. Once the twin stents have been deployed and the seal securely made, then the medication can be introduced through the catheter at a low pressure.

Figure 6:
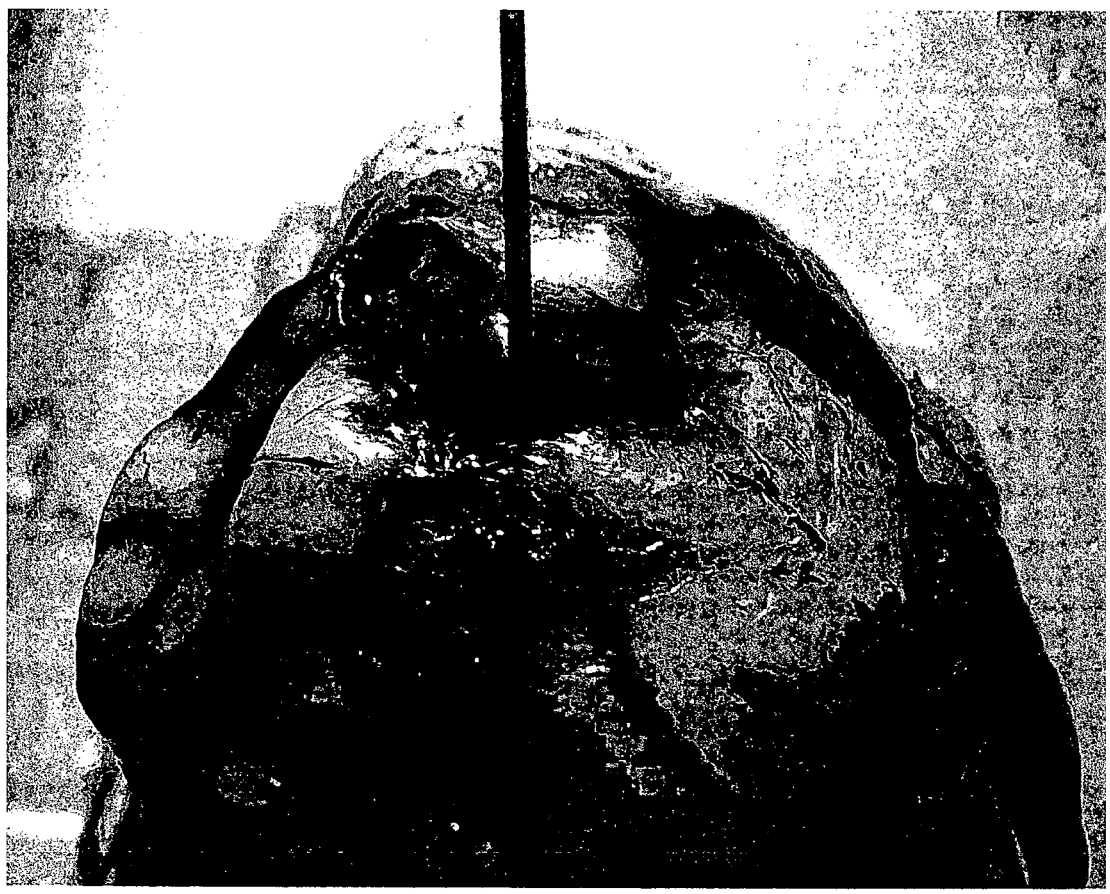
FIG. 6 shows leakage out of the pia when a conventional catheter is inserted into cortex
Figure 7:
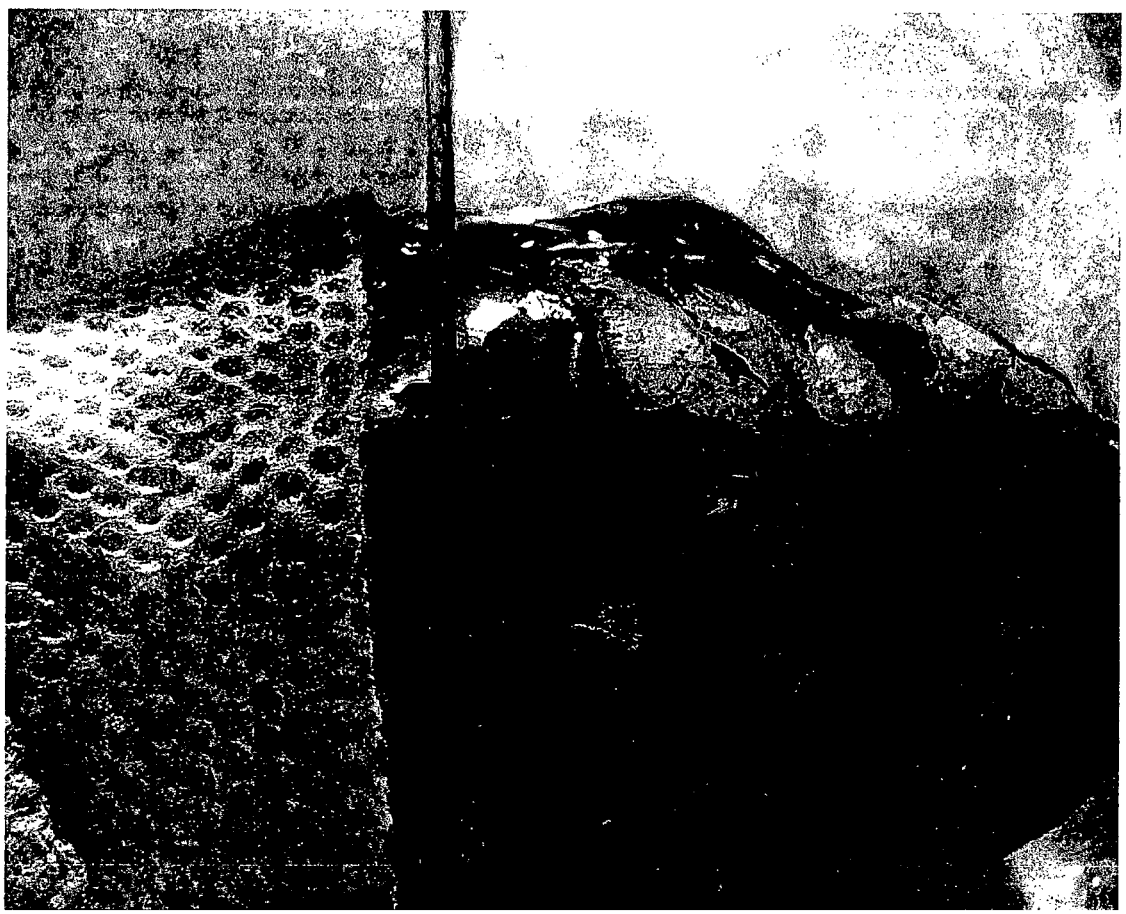
FIG. 7 illustrates the claim of FIG. 6 by showing staining of paper placed outside the pia

As illustrated in a control trial (FIGS. 6 and 7) the medication will normally be observed to flow back up the resistant edge of the catheter towards the surface of the cortex and the pia. However, since the hole in the pia made by the catheter is now sealed by the twin stents the medication forms a bolus contained by the pia and then quickly disperses over the cortical surface, in the space between the cortical surface and the pia in the desired manner without any additional external intervention. Again, the variations in design can be observed to determine their effects on actual process events and results.

Figure 8:
FIG. 8 shows spreading of dye underneath the pia upon using the twin-stent catheter, one of the embodiments of the current invention.

For the purpose of this test and demonstration, a small amount of air has been introduced with a dye through the catheter so that the photograph of FIG. 8 can clearly indicate the fact that the seal is airtight and that the dye is under the pia rather than having leaked out on top of it. In operational conditions, no air should be introduced, but it has previously been demonstrated that the medication would still disperse easily under the pia across the surface of the cortex.

Figure 9:
FIG. 9 illustrates the claim of FIG. 8 by showing that the paper placed outside the pia is now not stained.

To indicate that the dye had not leaked out onto the outer surface of the pia, a white paper tissue was laid over part of the dyed area to show that the outer surface of the pia remains dry (FIG. 9).

The above example indicates that even under direct visual observation, devices that seal the puncture about a catheter, such as the twin-stent catheter, are viable means by which to temporarily seal the puncture in a layer through which a catheter or needle is inserted, material delivered through the catheter or needle, and the puncture sealed (as with the pia) while materials such as medication is introduced. Even when working manually with a lightly-engineered mounting, its deployment was straightforward and reliably functional. The practicality of an operational production version should be apparent. The device can be easily manufactured and readily acceptable commercially. Improved designs for catheters and improved techniques can be determined and evaluated by non-invasive observation on live subjects also.

The Parasol Catheter:

A proprietary device in actuality created before the twin stent successfully used a "parasol catheter" for this purpose. It was deemed appropriate to identify that multiple different structures could be used to seal the puncture or hole from catheter needle introduction of materials through the pia and between the pia and the cortex. This maximises the options in design and likelihood of a fully functional operational design being developed.

Parasol Seal Catheter for Drug Delivery

The purpose of this catheter is to enable the introduction of a drug between the pia and the cortex or within the cortex while preventing back flow along the needle and past the pia.

The pia membrane is extremely delicate and vulnerable to physical damage, but is an effective physical barrier beyond which any introduced drug must consequently be placed. It is therefore generally necessary to pierce the pia membrane (and the other membranes outside it) with the catheter end in order to introduce the therapeutic drug. However, the normal flow-path that is created when the drug is introduced under pressure is back along the path of the catheter needle and out through the hole cut through the pia by the needle. This back-flow phenomenon results in a partial failure to introduce the drug and difficulty in determining the amount of drug that has actually been introduced.

The parasol seal catheter can address this problem after the tip of the catheter will pierce the dura and pia membranes.

Figure 10:
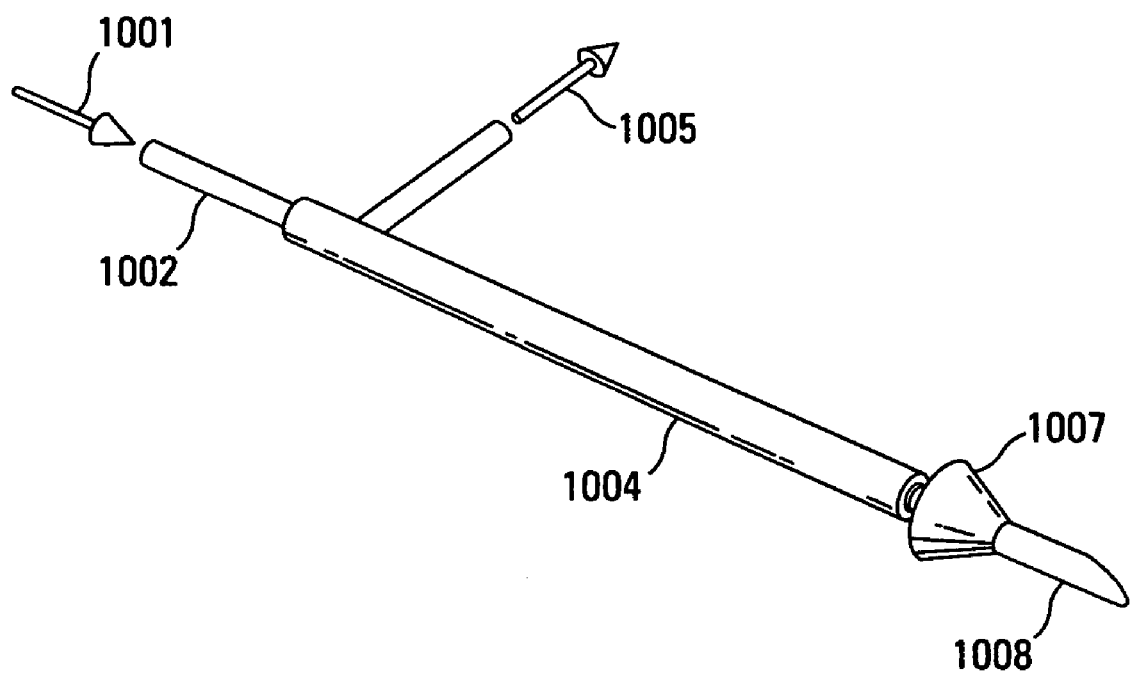
FIG. 10 shows the overall construction of the parasol catheter

FIG. 10 of P-S catheter

The catheter will ordinarily consist of concentric tubes, although parallel adjacent tubes or helixing tubes may also be used. In the specific design shown in FIG. X, there may be a space between the outer and inner tubes, located by internal spacing fins that will be used to generate slight suction. The protruding length of the inner tube will be variable, adjustable or fixed. Drug delivery preferably will be affected through the inner tube, although this is a design choice. The inner tube may have an area of reduced outside diameter near the piercing tip of the catheter in order to accommodate the folded 'parasol.' In place of the parasol, which displays a forward looking or rearward looking convex surface (preferably a sloped, curved, spherical or ellipsoidal surface) and an opposed rearward looking and forward looking opposed (respectively) concave surface (preferably a sloped, curved, spherical or ellipsoidal surface), one may use an inflatable or expansible balloon-type structure that would have the convex curved or sloped surfaces on both the forward looking and rearward looking sections of the balloon. By sloped is meant a not necessarily curved surface upon expansion of the balloon or parasol, but a shape that might be more pyramidal in geometry, with straight lines and edges.

FIG. 11

Figure 11:
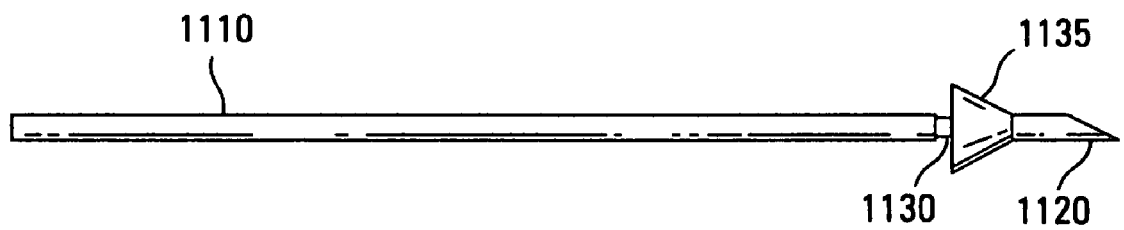
FIG. 11 shows the inner tube of the parasol catheter and how it accommodates the folded parasol

The parasol shown in FIG. 11 is shown to consist of a cone of an extremely thin membrane, the rim of which may be very slightly reinforced. The circumference of the truncated cone of the parasol membrane may be attached to the inner tube at the forward end of the parasol recess. When the catheter pierces the pia (or other first surface of the two opposed distinct surfaces), the piercing inner tube will be positioned so that the parasol is held just within the outer tube. When the tip of the outer tube rests against the outside of the dura the piercing inner tube will then be advanced so that the entire parasol just passes through the pia. Unrestrained by the outer tube the parasol, will open very slightly against the pressure of the surrounding matter. Only very slight deployment is necessary. Electronic or pneumatic control or enhancement of parasol deployment is also envisaged, which is a simple engineering effect.

FIG. 12

The piercing inner tube is then shown to be slightly withdrawn, collapsing the parasol back against the inside of the pia. The parasol membrane now covers the gap between the pierced edge of the hole in the pia and the needle, the outer diameter of the parasol being significantly greater than that of the piercing needle. Very gentle suction is now applied through the void within the outer tube, the reduced pressure drawing the dura and pia together and pulling the parasol membrane against the pia and into any gaps between the pia and the needle. It is also possible to have the parasol or balloon deployed on the first contacted side of the pia so that the seal is formed at a position on the proximal side of the pia, where the catheter first entered the tissue. This may be analogized to plugging a hole in the hull of a ship from inside the ship or outside the hull.

FIG. 13

The material or drug is then introduced through the (preferred) inner needle or lumen while reduced fluid pressure (suction) is continuously maintained through the outer tube. With the hole on the pia effectively sealed by the parasol membrane and the inner tube, the introduced drug will accumulate in the surface of the cortex and under the pia, rather than leaking out.

The normal back flow pattern means that the introduced drug will initially attempt to flow back along the outside of the needle to the surface of the cortex and the underside of the pia. However, where previously the drug would then leak out through the hole made in the pia by the piercing inner needle, the Parasol Seal Catheter would allow the drug to accumulate around the needle below the parasol, between the pia and the cortex. As the quantity of drug increases so this reservoir would spread outwards, bathing an increasing area of the surface of the cortex in the introduced drug.

Other Designs: Rifle, Double Rifle and Exterior Rifle

The objective of these alternative designs within the scope of the disclosed technology is to counter the tendency for back-flow of liquids injected through cortical catheters. While the Parasol and Twin-Stent designs are particularly appropriate where the desired location for the infusate is on the exterior surface of the cortex, the Rifle designs are primarily intended for the delivery of a bolus of medication anywhere within the brain regardless of its proximity to any physical barrier. There are at least three forms of Rifle catheter.

The Single Rifle form consists of a simple cannula, the inner surface of the tube forming the cannula being rifled by means of a spiral projection or groove that runs down its internal length. As the infusate passes slowly down the cannula the rifling imparts a twist to the flow of the liquid, creating a greater degree of directional flow stability that continues once it passes the distal tip of the cannula and enters the brain. This increased directional stability enables the flow to continue directly outwards from the cannula tip. This contrasts to the situation when a conventional un-rifled cannula is used, in which case the liquid normally reverses direction and flows back up the outside of the cannula.

Given the very limited rates of infusion and the consequently low velocity at which the infusate leaves the distal tip of the cannula, the directional stability of the flow is limited even when a Single Rifle cannula is used. This stability of flow varies significantly according to the nature of the infusate in question.

In cases where the directional stability of the infusate flow imparted by a Single Rifle cannula is insufficient to obviate back-flow, an additional measure may be used, in the form of a Double Rifle cannula. A Double Rifle cannula shares the interior spiral rifling typical of the Single Rifle in order to maximize the directional stability of the infusate flow, but has additional exterior rifling grooves along the exterior wall of the cannula. Simultaneous to the drug infusion via the interior of the cannula, saline solution is pumped along (up or down) the exterior rifling at a very slow rate and in a very small quantity. Any tendency for the infusate to flow back is defeated by the existing contrary or parallel flow of the saline solution, thus obliging or limiting the infusate to maintain its desired flow direction away from the distal tip into the brain. The informing logic of the exterior rifling of the Double Rifle cannula recognises that infused liquids will find an easier pathway formed against an available hard surface. Thus backflow occurs where the only available hard-surface path is back up the cannula towards the point of penetration. The direction of flow is determined by the availability of a hard-surface path, not by any identification or primacy of "back" or "forward" direction. In the Double Rifle case, the neutral saline solution infusate is preferably introduced along the cannula in a direction leading towards the interior of the brain. Any tendency of the drug being infused via the inside of the cannula to backflow will be discouraged by the (chemically neutral) liquid already flowing towards it down the external wall or filling the grooves. The infused drug will consequently have lost its easier hard-surface path and will be more inclined to flow in the desired direction outward from the distal tip, encouraged by the enhanced directional stability imparted by the rifling on the internal surface of the cannula. It may be argued that the rifling on the external wall of the cannula is unnecessary, that the saline infusate will anyway take the hard-surface path towards the distal tip. However, the rifling assists in creating surface adhesion between the saline infusate and the cannula, in minimising any tendency of the saline solution itself to flow back and in assisting the directional tendency of the infused drug from the distal tip.

In certain cases it may be desirable to minimise the size of the intrusion effected by a cannula. In this situation an Exterior Rifle cannula may be used. This consists of a cannula tube down which the infusate drug is pumped. Projecting from the distal tip of this tube is a solid needle, the outside of which is rifled. As the infusate emerges from the tube it takes the proffered hard-surface path down the outside of the rifled solid needle. When it reached the distal tip of the needle the liquid infusate cannot reverse back up the only existing hard-surface path, since this is blocked by the continuing flow of further infusate. Consequently the infusate forms a bolus, the direction imparted by the rifling causing it to locate slightly forward of the distal tip of the needle.

The NP3 Catheter Design

Figure 14:
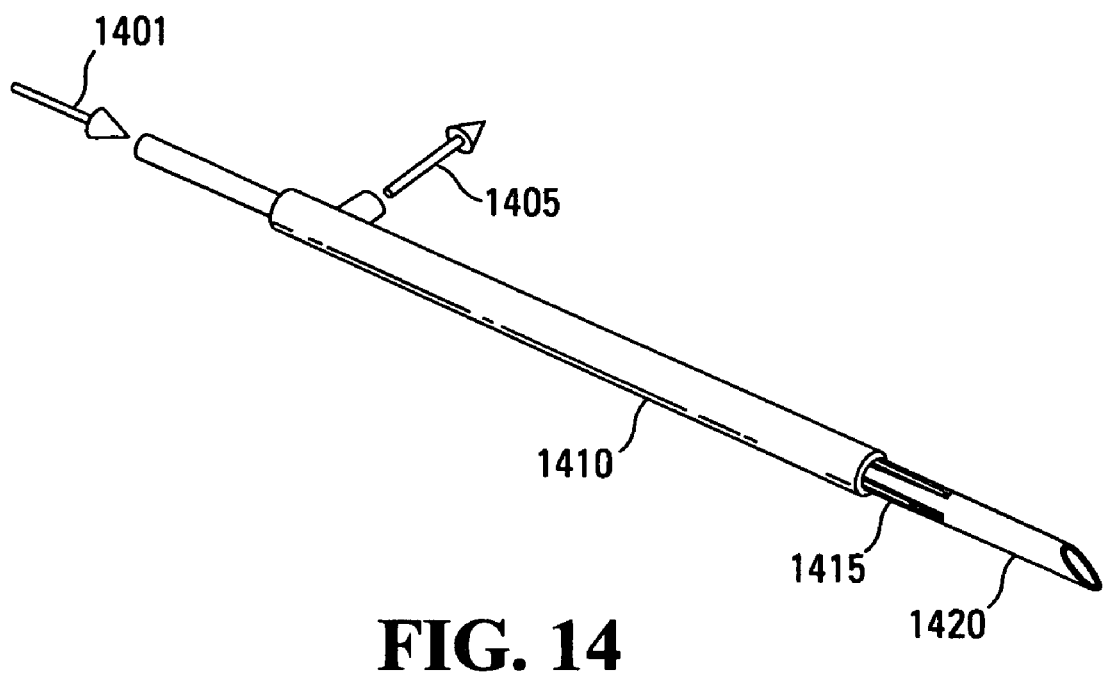
FIG. 14 shows a construction of the ventricle circulation catheter.

Ventricle Circulation Catheter for Drug Delivery (FIG. 14)

The intended purpose of this catheter design is to maintain the normal (e.g., cranial) pressure in a region of a patient while introducing material or drugs to the required region of the patient (e.g., cortex).

Increases in pressure within certain regions of anatomy, such as the brain, abruptly change the internal state, and may cause negative side effects. It is therefore desirable to discover the means to avoid any increase in pressure. Introducing drugs to the brain and thus increasing the volume of matter within it is likely to increase the internal pressure, regardless of how slow the introduction may be. The necessity of keeping the pressure level down is likely to lead to slower introduction than might otherwise be desirable or necessary, thus increasing the time required for the therapy and thus the risk of other problems arising.

The previously mentioned and now greater explained NP3 catheter will be introduced into the cortex, for example from the ventricle.

This embodiment of the catheter will be constructed from concentric tubes. Drug delivery under positive pressure will be through the inner tube. Negative or relatively reduced pneumatic (suction) pressure will be maintained in the gap between the inner tube and the outer tube. Fins, struts, (continuous or discontinuous) supports or splines running out along the longitudinal axis from the working end of the outer tube will maintain the relationship between the two tubes. The supports (e.g., fins) will also serve to create spaces between the inner tube and the membranes that it has pierced in order that the liquid can flow from the positive pressure at the piercing end of the inner tube back to the negative pressure at the end of the outer tube that remains outside the membrane pierced by the inner tube, as shown in FIG. 14.

Outside the cranium a pump connects the two tubes so that liquid circulates within the brain, coming out of the end of the piercing inner tube then back towards and into the open end of the outer tube. Within the catheter the liquid then passes up the outer tube, through the external pump and back down the piercing tube again.

The material or drug is introduced in a liquid form and metered at an external pump. Because liquid is being removed in direct proportion to its introduction, the increase in pressure is kept to a minimum, thus reducing the risk of therapy-induced trauma.

The length of the piercing inner tube projecting beyond the end of the fins can be adjusted or selected or modified (e.g., by initial design or in situ) according to the depth beyond the membrane that the drug should be delivered. Since the catheter makes use of backflow and even augments it by pneumatic pressure control (e.g., suction), the primary distribution will be around and along the penetrating length of the piercing inner tube.

Pressure-Equalising Cortical Catheter Model: Operating Instructions for Testing

Any significant increase in pressure within certain portions or regions of the body, such as the cortex, can trigger adverse physiological effects. The introduction of additional liquids will normally increase such pressure, restricting the volume of medication that can be introduced during a single procedure. The intention of this catheter design is to minimise changes in (e.g., cerebral) pressure by balancing the pressure caused by the introduction of medication by the removal of an equal amount of (cerebral) fluid.

Medication is introduced through the tip of the catheter, resulting in positive pressure locally. Flow patterns in this context are primarily back along the catheter needle and the puncture created by it. Introduced fluid under pressure will normally be expressed through the puncture in the pia, thus making metering of the medication inaccurate. The vents at the base of the catheter needle allow the creation of negative pressure, thus encouraging the flow of medication from needle tip to needle base but reducing the risk of leakage through the hole in the pia. Near normal pressure is thus maintained within the cortex.

A metered medication reservoir will allow measurement of the dose delivered, even if it circulates for a period before being absorbed. Although some additional pressure is created by the addition of the medication, this will be kept to a minimum because the lack of leakage means that no excess dose needs to be delivered to allow for wastage. If zero pressure increase is necessary this could be achieved by the removal of an amount of cortical fluid equal to the volume of medication that is added. (In this case there should not be simple circulation of fluids.) The distance between needle tip and the vents is adjustable, thus controlling the depth to which medication is administered.

The present catheter model is probably larger than an operational version and has not been made to scale, but this is only an issue of scale. The limited purpose of the model is to allow initial tests of the underlying principle of the design and to direct subsequent development of the design.

For constructional convenience, the model is constructed from stainless steel, which would not be the case for an operational version. The prototype model has been made entirely by hand and therefore contains a level of inaccuracy and roughness which would not be the case in a more advanced operational prototype. For example, the slots might be cut by laser instead of with a hand saw.

For more effective laboratory testing purposes one or two adjustable pumps, a medication reservoir and one or two pressure gauges will need to be available. A large scale simulation of the dura and pia with cortical fluid contained beneath them will need to be constructed, for example by using a vessel containing a slightly thickened liquid covered by saran wrap (cling film) that is in direct contact with the liquid it encloses.

The body of the catheter may consist of a long tube (a) with a shorter tube (b) attached at right angles near the top end. A 'stop' ring (c) is attached to the lower extreme of the main body tube in order to limit the penetration of the catheter into the pia and soft tissue of the brain. Also at the lower end a smaller diameter tube protrudes (d), which has longitudinal vent slots cut in it through which the negative pressure will be created.

Near the top of the main body tube and at a right angle to it a short lateral tube is attached (b). This is the negative exit to which a flexible tube leading to the negative side of an external pump will be attached. Above a lateral weld groove in the main body tube, lying in the same axis, is a short section of tube containing a silicon grommet (e) that seals the main body chamber to prevent any loss of negative pressure within the body and to grip the catheter needle (f) in the required position.

Catheter needle: The catheter needle (f) passes within the full length of the main body, centred by the vents at the lower end and the silicon seal at the top end. At the top end of the catheter needle are welded concentric larger tubes (g) to increase the diameter to one to which can be attached a tube leading to an external medication reservoir and from there to the positive pressure side of the external pump.

The length of catheter needle protruding from the vents at the lower end of the main body can be adjusted by grasping the top, large tube, end of the needle and pushing or pulling it firmly through the main tube against the grip of the silicon grommet. While the needle can be fully removed from the main body, repeated re-insertion will damage the silicon seal. Unless there is a specific problem that requires removal of the catheter needle from the main body it is therefore recommended to avoid doing so.

Operating the Catheter the inlet (positive pressure) tube on the catheter needle is connected to the external medication reservoir, which is in turn connected to the outlet of the external pump. The outlet (negative pressure) tube (b) is connected to the inlet tube on the external pump. The catheter needle (f), connecting tubes, reservoir and pump(s) should be filled with liquid and without air. The needle length is adjusted by pushing or pulling the needle through the main body of the catheter.

The catheter needle is pushed through the saran wrap barrier (pia) until the vent slots (d) also penetrate, the stop ring (c)

resting gently against the barrier. Gradually, positive pressure is introduced by the introduction of 'medication,' balanced as closely as possible by negative pressure at the vents slots. Since the liquid to be circulated will have a certain viscosity, the pressure should only gradually be increased so that the flow is initiated before significant pressure is generated.

Introduction/circulation of the medication should continue until the entire dosage has been passed beyond the saran wrap barrier. If medication is returning to the reservoir before the full dose is delivered then circulation might be continued until the 'cortex' has absorbed it all.

The catheter should be carefully rinsed after each test so that the fine vent holes do not become blocked.

The following tables can assist in reading the various figures, with the numbers shown in the figures relating to various elements of the structures.

| FIG. 1 | |
| --- | --- |
| Catheter | 100 |
| Adjustment | 101 |
| Thread | 103 |
| Casing | 105 |
| Washer | 107 |
| Stents | 108 |
| Needle tip | 109 |

| FIG. 2 | |
| --- | --- |
| Casing | 202 |
| Adjuster | 205 |
| Thread | 207 |
| Spring | 209 |
| Catheter | 200 |
| Washer | 210 |
| Stents | 212 |
| Needle tip | 214 |

| FIG. 4 | |
| --- | --- |
| Catheter | 400 |
| Adjustment | 402 |
| Casing | 404 |
| Stent | 405 |
| Stent | 406 |
| Pia | 408 |
| Needle tip | 410 |

| FIG. 5 | |
| --- | --- |
| Catheter | 500 |
| Casing | 501 |
| Adjustment | 502 |
| Pia | 504 |
| Needle tip | 506 |
| Stents open | 508 |

| FIG. 10 | |
| --- | --- |
| Inflowing liquid | 1001 |
| Inner tube | 1002 |
| Outer tube | 1004 |
| Suction | 1005 |
| Parasol | 1007 |
| Piercing tube | 1008 |

| FIG. 11 | |
| --- | --- |
| Inner tube | 1110 |
| Piercing tube | 1120 |
| Parasol recess | 1130 |
| Parasol | 1135 |

Figure 12:
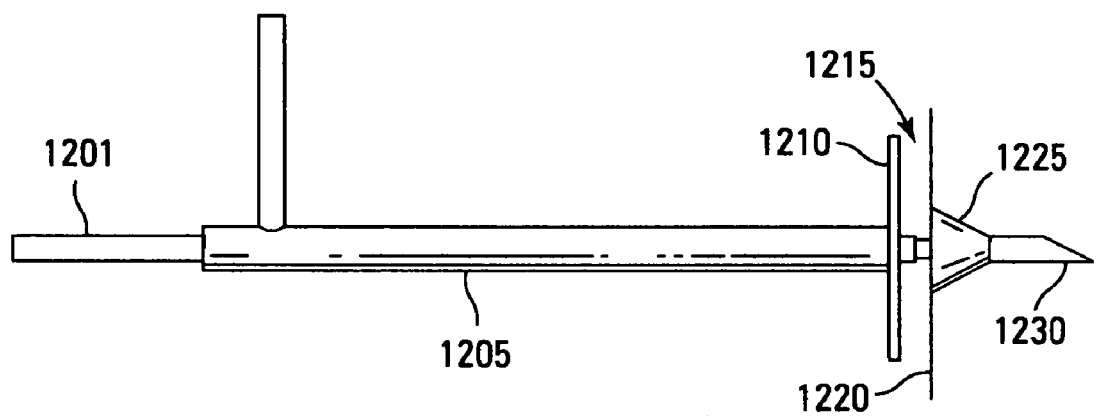
FIG. 12 shows an intermediate stage of operation of the parasol catheter showing the liquid between the opposed layers as described in the invention.

| FIG. 12 | |
| --- | --- |
| Inner tube | 1201 |
| Outer tube | 1205 |
| Dura membrane | 1210 |
| Liquid | 1215 |
| Pia membrane | 1220 |
| Parasol | 1225 |
| Piercing tube | 1230 |

Figure 13:
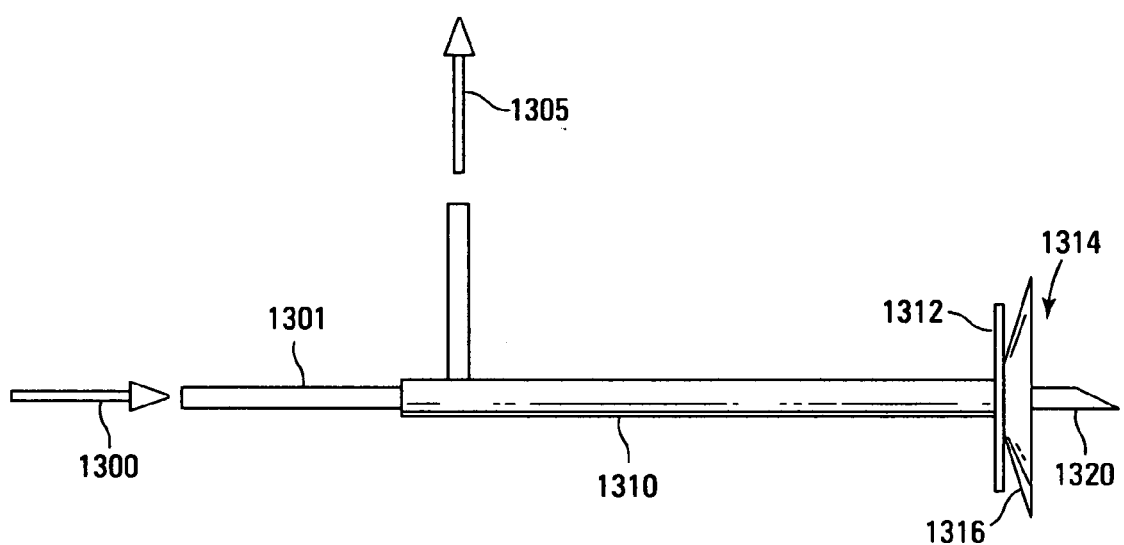
FIG. 13 shows the parasol catheter sealing the pia.

| FIG. 13 | |
| --- | --- |
| Drug in | 1300 |
| Inner tube-partially withdrawn | 1301 |
| Suction | 1305 |
| Outer tube | 1310 |
| Dura membrane | 1312 |
| Pia membrane | 1314 |
| Collapsed parasol | 1316 |
| Piercing tube | 1320 |

| FIG. 14 | |
| --- | --- |
| From pump | 1401 |
| To pump | 1405 |
| Outer tube | 1410 |
| Fins | 1415 |
| Piercing inner tube | 1420 |

Figure 15:
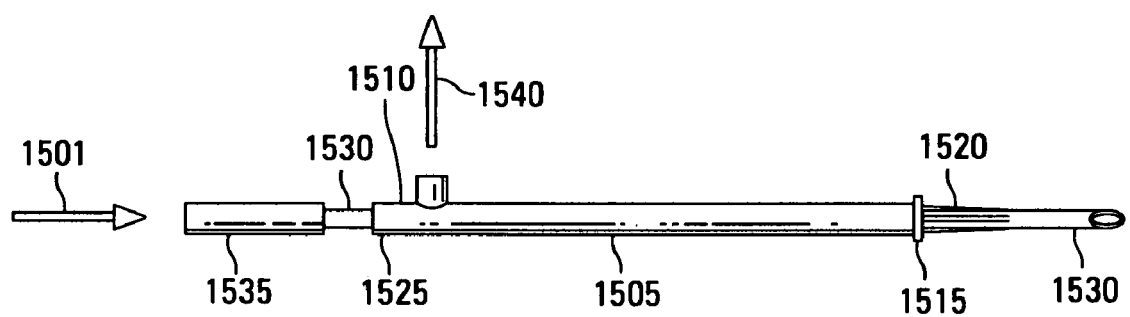
FIG. 15 shows a construction of the pressure-equalization catheter.

| FIG. 15 | |
| --- | --- |
| From pump | 1501 |
| Main body | 1505 |
| Short lateral tube | 1510 |
| Stop ring | 1515 |
| Vent slots tube | 1520 |
| Internal silicon grommet | 1525 |
| Catheter needle | 1530 |
| Larger catheter tube end | 1535 |
| To pump | 1550 |

It should be noted with respect to the earlier described Published U.S. Patent Application No. 20030097116 (Putz, David A.) that there is another distinction as between this disclosure and the present technology. The Putz assembly ensures delivery of the drug to the selected site by providing a barrier which prevents "backflow" or leakage of the drug. The assembly includes a guide catheter having an inflatable balloon which is able to seal or occlude the tract created by the insertion of the guide catheter into the brain. The guide catheter further includes a passageway which receives a delivery catheter through which the drug is administered to the selected site in the brain. This is distinct from the action of the present technology in which a shape is distorted and not inflated (that is there may be less than 10%, less than 5% and less than 25 down to 0%, change in volume of the present system, which is not inflation as performed by Putz). The present system also operates to trap the delivered material between existing layers and not to block only backflow. With inflation within the opening or hole, the inflation places outward pressure (radial pressure) against the edges of the hole itself, likely to propagate the tearing of the hole. This is in contrast with the technology described herein where distortion or even inflation on opposed sides of the opening but not within the opening to any extent, would seal the hole around the edges by pressure on both sides of the hole confining the edges of the hole perpendicular to the surfaces of the tissue rather than radially within the hole.

Alternative designs, alternative materials, and the use of non-invasive imaging techniques (e.g., MR, sonogram, fluoroscopy, etc.) may be used to determine and evaluate procedural and structure variations for various treatments. Specific treatment planning should be developed for procedures and for specific patients.

What is claimed:

1. A method for the provisioning and positioning of a flowable material selected from the group consisting of a flowable drug medication material into a region of a patient comprising:

identifying a region of a patient to be viewed or treated;

identifying a region between the pia and the cortex wherein the region forms a potential volume between two opposed different and distinct tissue surfaces;

penetrating at least one of the two opposed different and distinct tissue surfaces selected from the pia and the cortex with a flowable drug medication material delivery device; and providing flowable material from the flowable drug medication material delivery device into the potential volume between the pia and the cortex to create a volume containing at least delivered flowable drug medication material between the at least two different and distinct tissue surfaces; and performing a medical procedure of delivery of the drug medication;

wherein the material delivery device forms an at least partial seal around the entire puncture formed by penetration of only one of the at least two opposed different and distinct tissue surfaces;

wherein the seal is formed covering a surface area extending away from and entirely around a diameter of the material delivery device immediately adjacent the pia or the cortex.

2. The method of claim 1 wherein the volume is mass transfer stable in that less than 80% by volume of delivered material is removed from the created volume by natural biological activity in less than 5 minutes and a non-invasive visual examination selected from the group consisting of MRI, PET or fluoroscopy is used during penetration of the at least one of the two opposed surfaces or while providing the flowable drug medication material to create the volume.

3. The method of claim 1 wherein the seal is formed on both sides of the puncture relative to the only one of the at least two opposed different and distinct tissue surfaces penetrated.

4. The method of claim 1 wherein a structure forming the seal is inflated to assist in sealing the puncture and the seal is circumferentially around the puncture.

5. The method of claim 1 wherein a structure forming the seal is flexible and distorts to apply pressure over the puncture.

6. The method of claim 1 wherein the seal is formed by expansion of a component on the material delivery device around a region of the puncture created by the penetration.

7. The method of claim 1 wherein there is a second seal formed against at least one surface in addition to the pia.

8. A method for the provisioning and positioning of a flowable medication material comprising a medical drug into a region of a patient comprising:

identifying a region of a patient between the pia and the cortex to be viewed or treated;

identifying a region wherein the region forms a potential volume between two opposed different and distinct tissue surfaces consisting of the pia and the cortex;

penetrating at least one of the two opposed different and distinct tissue surfaces with a flowable material delivery device; and providing the flowable material delivery device into the potential volume to create a volume containing at least delivered flowable material between the at least two different and distinct tissue surfaces;

wherein the material delivery device forms an at least partial seal around a puncture formed by penetration of only one of the at least two opposed pia and cortex surfaces; and performing a medical procedure consisting essentially of delivery of the medical drug; and wherein the seal is formed covering a surface area extending circumferentially away from and entirely around a diameter of the material delivery device immediately adjacent the pia or the cortex.

9. The method of claim 8 wherein an amount of cortical fluid is removed while flowable material is delivered to minimize pressure increases in local fluids.

10. The method of claim 9 wherein the seal is formed on both sides of the puncture relative to the only one of the at least two opposed different and distinct tissue surfaces penetrated.

11. The method of claim 8 wherein an amount of cortical fluid is removed while flowable material is delivered so that there is a zero pressure increase in cortical fluids.

* * * * *